United States Patent [19]
Dove et al.

[11] Patent Number: 5,925,523
[45] Date of Patent: Jul. 20, 1999

[54] INTRACTION TRAP ASSAY, REAGENTS AND USES THEREOF

[75] Inventors: Simon Dove, Cambridge; J. Keith Joung, Winchester; Ann Hochschild, Brookline, all of Mass.

[73] Assignee: President & Fellows of Harvard College, Cambridge, Mass.

[21] Appl. No.: 08/920,015

[22] Filed: Aug. 26, 1997

Related U.S. Application Data

[63] Continuation-in-part of application No. 08/918,612, Aug. 22, 1997, abandoned.
[60] Provisional application No. 60/024,484, Aug. 23, 1996.
[51] Int. Cl.⁶ .............................. C12Q 1/68; C12Q 1/02
[52] U.S. Cl. ................................... 435/6; 435/29
[58] Field of Search ............................ 435/4, 6, 7.1, 7.2, 435/7.32, 7.33, 7.34, 7.35, 7.37, 29

[56] References Cited

U.S. PATENT DOCUMENTS 5,283,173   2/1994   Fields et al. ................................ 435/6

FOREIGN PATENT DOCUMENTS

WO 94/10300   5/1994   WIPO .

OTHER PUBLICATIONS

Stanley Fields and Song, "A novel genetic system to detect protein–protein interactions",Nature(1989), 340: 245–246, Jul., 20, 1989.

Roger Brent et al,"A Eukaryotic transcriptional activator bearing the DNA specificity of a Prokaryotic repressor", Cell (1985) 43: 729–736, Dec. 1985.

Ma et al, "Converting a Eukaryotic transcriptional inhibitor into activator",CELL(1988),55: 443–446, Nov., 4, 1988.

Chien et Al. "The two–hybrid system: A method to identify and clone genes for protein that interact with a protein of interest",PNAS,(1991)88:9578–82, Nov. 1991.

Durfee et al. "The retinoblastoma protein associates with the protein phosphatase type 1 catalyitic subunit". Genes & Development (1993) 7:555–69, Dec. 18, 1992.

Gyuris et al. "Cdi1, a human G1 and S phase protein phosphatase that associates with Cdk2",Cell (1993),75:791–803, Nov. 19, 1993.

Vojtek et al."Mammalian Ras interacts directly with the Serine/Threonine kinase Raf.";Cell(1993), 74: 205–214, Jul. 16, 1993.

Golemis et al. "Fused Protein Domains inhibit DNA Binding by LexA", Mol. Cell. Biol. (1992),12:3006–3014, Jul. 1992.

Ebina et al. "LexA Protein is a Repressor of the Colicin El Gene*", J.Biol. Chem. (1983),258:13258–13261,Nov.10, 1983.

Harper et al. "The p21 Cdk–interacting Protein Cip1 is a potent inhibitor of G1 Cyclin–Dependent Kinases." CELL19930,75:805–816, Nov. 19, 1993.

Silver et al. "Techniques for cloning cDNAs encoding interactive transcriptional regulatory proteins.", Mol. Biol. Rep.(1993), 17: 155–165, Oct. 5, 1992.

Yang et al. "A protein Kinase Substrate identified by the Two–Hybrid system.", Science (1992), 257:680–685,Jul. 31, 1992.

Luban et al. "Human immunodeficiency virus Type 1 Gag Protein binds to Cyclophilins A and B.", Cell (1993), 73:1067–1078.

Hardy et al. "A RAP1–interacting protein involved in transcriptional silencing and telomere length regulation." Genes Devel. (1992), 6:801–814.

Bartel et al. "Elimination of false positives that arise in using the Two–Hybrid system." Biotechniques (1993), 14: 920–924.

Li et al. "Identification of mutations in p53 that affect its binding to SV40 large T antigen by using the yeast two–hybrid system." FASEB J. (1993), 7:957–963.

Lalo et al. "Interactions betweeen three common subunits of yeast RNA polymerases I and III." PNAS (1993), 90:5524–5528, Feb. 8, 1993.

Jackson et al. "Cell cycle regulation of the yeast Cdc7 Protein Kinase by Association with the Dbf4 protein." Mol. Cell. Biol. (1993), 13:2899–2908, May 1993.

Madura et al. "N–recognin/Ubc2 Interactions in the N–end Rule Pathway*." J.Biol. Chem. (1993),268:12046–12054, Jun. 5, 1993.

Iwabuchi et al. "Use of the two–hybrid system to identify the domain of p53 involved in oligomerization." Oncogene (1993), 8:1693–1696.

Ebright et al . "The *Escherichia coli* RNA polymerase *alpha* subunit: structure and function." Curr Opin Genet (1995), 5: 197–203.

Himmelfarb et al. "GAL11P : A yeast Mutation that potentiates the effect of weak GAL4–Derived activators." CELL (1990), 63: 1299–1309.

Severino et al. "Assembly of functional *Escherichia coli* RNA polymerase containing β (beta) subunit fragments." Proceedings of the national Academy of Science (1995), 92:4591–4595.

Gentry et al. "The cloning and sequence of the gene encoding the omega subunit of *Escherichia coli* RNA polymerase." Gene (1986), 48:33–40.

Deora et al. "Purification and Characterization of DNA dependent RNA Polymerase from staphylococcus aureus." Biochem Biophys Res Commun (1995), 208: 610–616.

Barberis et al. "Contact with a component of a polymerase II Holoenzyme Suffices for gene Activation", Cell, vol.81, 1995, pp. 359–368.

(List continued on next page.)

*Primary Examiner*—Nancy Degen
*Assistant Examiner*—Robert Schwartzman
*Attorney, Agent, or Firm*—Matthew P. Vincent; Beth E. Arnold; Foley, Hoag & Eliot, LLP

[57] ABSTRACT

The present invention makes available an interaction trap system (hereinafter "ITS") which is derived using recombinantly engineered prokaryotic cells.

36 Claims, 8 Drawing Sheets

OTHER PUBLICATIONS

Chatterjee and Struhl: "Connecting a promoter–bound protein to TBP bypasses the need for a transcriptional activation domain", Nature, vol. 374, 1995, pp. 820–822.

Ishihama: "Protein–protein communication within the transcription apparatus", Journal of Bacteriology, vol. 175, No 9, 1993, pp. 2483–2489.

Dove et al: "Activation of Prokaryotic transcription through arbitrary protein–protein contacts", Nature, vol. 386, 1997, pp. 627–630.

Jacob et al. (1993) Construction of chimeric proteins from the sigma N–associated transcriptional activators VnfA and AnfA of Azotobacter vinelandii shows that the determinants of promoter specificity lie outside the 'recognition' helix of the HTH motif i, 1993.

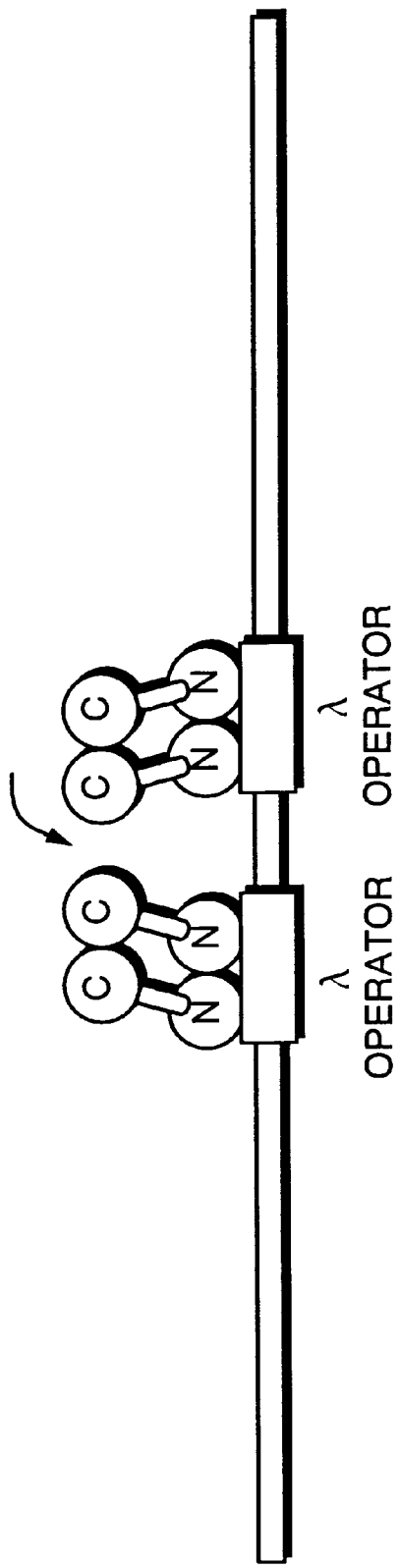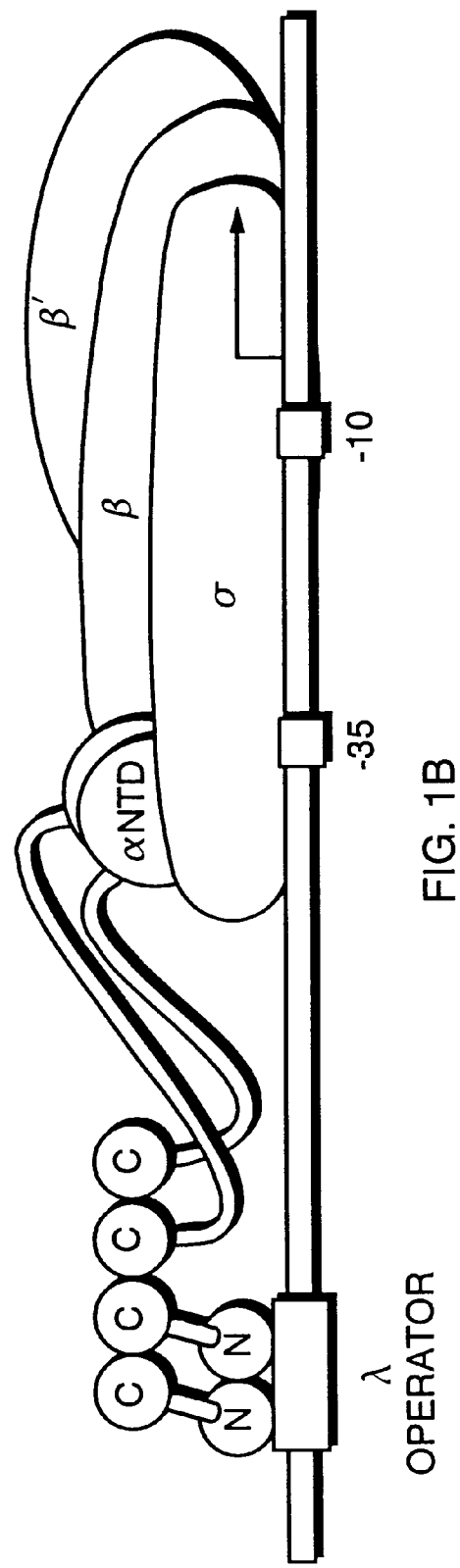

INTRACTION TRAP ASSAY, REAGENTS AND USES THEREOF

RELATED APPLICATIONS

This application is a continuation-in-part of U.S. patent application Ser. No. 08/918,612, filed on Aug. 22, 1997, abandoned, which claims the benefit of U.S. Provisional patent application No. 60/024,484, filed Aug. 23, 1996, both of which are incorporated herein by reference.

FUNDING

Work described herein was supported by National Institutes of Health Grant. The United States Government has certain rights in the invention.

BACKGROUND OF THE INVENTION

Specific protein-protein interactions are fundamental to most cellular functions. Polypeptide interactions are involved in, inter alia, formation of functional transcription complexes, signal transduction pathways, cytoskeletal organization (e.g., microtubule polymerization), polypeptide hormone receptor-ligand binding, organization of multisubunit enzyme complexes, and the like.

Investigation of protein-protein interactions under physiological conditions has been problematic. Considerable effort has been made to identify proteins that bind to proteins of interest. Typically, these interactions have been detected by using co-precipitation experiments in which an antibody to a known protein is mixed with a cell extract and used to precipitate the known protein and any proteins which are stably associated with it. This method has several disadvantages, such as: (1) it only detects proteins which are associated in cell extract conditions rather than under physiological, intracellular conditions, (2) it only detects proteins which bind to the known protein with sufficient strength and stability for efficient co-immunoprecipitation, (3) it may not be able to detect oligomers of the target, and (4) it fails to detect associated proteins which are displaced from the known protein upon antibody binding. Additionally, the precipitation techniques at best provide a molecular weight as the sole identifying characteristic. For these reasons and others, improved methods for identifying proteins which interact with a known protein have been developed.

One approach has been to use a so-called interaction trap system (also referred to as the "two-hybrid assay") based in yeast to identify polypeptide sequences which bind to a predetermined polypeptide sequence present in a fusion protein (Fields and Song (1989) Nature 340:245). This approach identifies protein-protein interactions in vivo through reconstitution of a eukaryotic transcriptional activator.

The interaction trap systems of the prior art are based on the finding that most eukaryotic transcription activators are modular. Brent and Ptashne showed that the activation domain of yeast GAL4, a yeast transcription factor, could be fused to the DNA binding domain of E. coli LexA to create a functional transcription activator in yeast (Brent et al. (1985) Cell 43:729–736). There is evidence that transcription can be activated through the use of two functional domains of a transcription factor: a domain that recognizes and binds to a specific site on the DNA and a domain that is necessary for activation. The transcriptional activation domain is thought to function by contacting other proteins involved in transcription. The DNA-binding domain appears to function to position the transcriptional activation domain on the target gene that is to be transcribed. These and similar experiments (Keegan et al. (1986) Science 231:699–704) formally define activation domains as portions of proteins that activate transcription when brought to DNA by DNA binding domains. Moreover, it was discovered that the DNA binding domain does not have to be physically on the same polypeptide as the activation domain, so long as the two separate polypeptides interact with each other. (Ma et al. (1988) Cell 55:443–446).

Fields and his coworkers made the seminal suggestion that protein interactions could be detected if two potentially interacting proteins were expressed as chimeras. In their suggestion, they devised a method based on the properties of the yeast Gal4 protein, which consists of separable domains responsible for DNA-binding and transcriptional activation. Polynucleotides encoding two hybrid proteins, one consisting of the yeast Gal4 DNA-binding domain fused to a polypeptide sequence of a known protein and the other consisting of the Gal4 activation domain fused to a polypeptide sequence of a second protein, are constructed and introduced into a yeast host cell. Intermolecular binding between the two fusion proteins reconstitutes the Gal4 DNA-binding domain with the Gal4 activation domain, which leads to the transcriptional activation of a reporter gene (e.g., lacZ, HIS3) which is operably linked to a Gal4 binding site.

All yeast-based interaction trap systems in the art share common elements (Chien et al. (1991) PNAS 88:9578–82; Durfee et al. (1993) Genes & Development 7:555–69; Gyuris et al. (1993) Cell 75:791–803; and Vojtek et al. (1993) Cell 74:205–14). All use (1) a plasmid that directs the synthesis of a "bait": a known protein which is brought to DNA by being fused to a DNA binding domain, (2) one or more reporter genes ("reporters") with upstream binding sites for the bait, and (3) a plasmid that directs the synthesis of proteins fused to activation domains and other useful moieties ("prey"). All current systems direct the synthesis of proteins that carry the activation domain at the amino terminus of the fusion, facilitating the expression of open reading frames encoded by, for example, cDNAs.

The prior art systems differ in their specifics. These details are typically relevant to their successful use. Baits differ in their DNA binding domains. For example, systems use baits that contain native E. coli LexA repressor protein (Durfee et al. (1993) Genes & Development 7:555–69; Gyuris et al. (1993) Cell 75:791–803). LexA binds tightly to appropriate operators (Golemis et al. (1992) Mol. Cell. Biol. 12:3006–3014; Ebina et al. (1983) J. Biol. Chem. 258:13258–13261), and carries a dimerization domain at its C terminus (Brent R. (1982) Biochimie 64:565–569; Little J et al. (1982) Cell 29:11–22; and Thliveris et al. (1991) Biochimie 73:449–455). In yeast, LexA and most LexA derivatives enter the nucleus, but are not necessarily nuclear localized. Others use baits that contain a portion of the yeast GAL4 protein (Chien et al. (1991) PNAS 88:9578–82; Durfee et al. (1993) Genes & Development 7:555–69; and Harper et al. (1993) Cell 75:805–16). This portion, encoded by residues 1–147, is sufficient to bind tightly to appropriate DNA binding sites, localize fused proteins to the nucleus, and direct dimerization; it also contains a domain that weakly activates transcription in mammalian cell extracts in vitro, and it is thus conceivable that this domain may increase transcription resulting from weakly interacting proteins.

Reporter genes differ in the phenotypes they confer. The products of some reporter genes (e.g., HIS3, LEU2) allow cells expressing them to be selected by growth on appropriate media, while the products of others (e.g. lacZ) allow cells expressing them to be visually screened. Reporters also differ in the number and affinity of upstream binding sites (e.g., lexA operators) for the bait, and in the position of these sites relative to the transcription startpoint (Gyuris et al., supra). Finally, they differ in the number of molecules of the reporter gene product necessary to score the phenotype. These differences affect the strength of the protein interactions the reporters can detect.

Preys differ in the activation domains they carry, and in whether they contain other useful moieties such as nuclear localization sequences and epitope tags. Some activation domains are stronger than others. Although strong activation domains should allow detection of weaker interactions, their expression can also harm the cell due to poorly understood transcriptional effects, either by titration of cofactors necessary for transcription of other genes ("squelching") (Gill et al. (1988) *Nature* 334:721–724) or by toxic effects that result when strong activation domains are brought to DNA (Berger et al. (1990) *Cell* 61:1199–208). Thus, it is possible that strong activation domains may prevent detection of some interactions. Prey proteins also differ in whether they are expressed constitutively, or conditionally. Conditional expression allows the transcription phenotypes obtained in selections (or "hunts") for interactors to be ascribed to the synthesis of the tagged protein, thus reducing the number of false positive cells that grow because their reporters are aberrantly transcribed.

Although most two hybrid systems use yeast, there are also mammalian variants. In one, interaction of VP 16 derivatives with a Gal4-derived bait drives expression of reporters that direct the synthesis of Hygromycin B phosphotransferase, Chloramphenicol acetyltransferase, or CD4 cell surface antigen (Fearon et al. (1992) *PNAS* 89:7958–62). In the other, interaction of VP16-tagged derivatives with Gal4-derived baits drives the synthesis of SV40 T antigen, which in turn promotes the replication of the prey plasmid, which carries an SV40 origin (Vasavada et al. (1991) *PNAS* 88:10686–90).

Several industrially significant uses of two hybrid systems have emerged. One use is to identify new protein targets for pharmaceutical intervention. Typically, the two-hybrid method is used to identify novel polypeptide sequences which interact with a known protein (Silver et al. (1993) *Mol. Biol. Rep.* 17:155; Durfee et al. (1993) *Genes Devel.* 7:555; Yang et al. (1992) *Science* 257:680; Luban et al. (1993) *Cell* 73:1067; Hardy et al. (1992) *Genes Devel.* 6; 801; Bartel et al. (1993) *Biotechniques* 14:920; and Vojtek et al. (1993) *Cell* 74:205). Variations of the two-hybrid method have been used to identify mutations of a known protein that affect its binding to a second known protein (Li B and Fields S (1993) *FASEB J.* 7:957; Lalo et al. (1993) *PNAS* 90:5524; Jackson et al. (1993) *Mol. Cell. Biol.* 13:2899; and Madura et al. (1993) *J. Biol. Chem.* 268:12046). Two-hybrid systems have also been used to identify interacting structural domains of two known proteins (Bardwell et al. (1993) *Med. Microbiol.* 8:1177; Chakraborty et al. (1992) *J. Biol. Chem.* 267:17498; Staudinger et al. (1993) *J. Biol. Chem.* 268:4608; and Milne et al. (1993) *Genes Devel.* 7:1755) or domains responsible for oligomerization of a single protein (Iwabuchi et al. (1993) *Oncogene* 8:1693; Bogerd et al. (1993) *J. Virol.* 67:5030). Variations of two-hybrid systems have been used to study the in vivo activity of a proteolytic enzyme (Dasmahapatra et al. (1992) *PNAS* 89:4159).

SUMMARY OF THE INVENTION

The present invention provides methods and reagents for practicing various forms of an interaction trap assay using prokaryotic host cells, e.g., bacterial cells.

For example, one aspect of the present invention relates to a method for detecting interaction between a first test polypeptide and a second test polypeptide. The method comprises a step of providing an interaction trap system including a prokaryotic host cell which contains a reporter gene operably linked to a transcriptional regulatory sequence which includes a binding site ("DBD recognition element") for a DNA-binding domain. The cell is engineered to include a first chimeric gene which encodes a first fusion protein, the first fusion protein including a DNA-binding domain and first test polypeptide. The cell also includes a second chimeric gene which encodes a second fusion protein including an activation tag (such as a polymerase interaction domain [PID]) and a second test polypeptide. Interaction of the first fusion protein and second fusion protein in the host cell activates transcription of the reporter gene, e.g., results in measurably greater expression of the reporter gene. Accordingly, the method also includes the steps of measuring expression of the reporter gene, and, generally, comparing the level of expression of the reporter gene to a level of expression in a control interaction trap system. A statistically significant increase in the level of expression is indicative of an interaction between the first and second test polypeptide portions of the fusion proteins.

Another aspect of the present invention relates to a kit for detecting interaction between a first test polypeptide and a second test polypeptide. The kit can include a first vector for encoding a first fusion protein ("bait fusion protein"), which vector comprises a first gene including (1) transcriptional and translational elements that direct expression in a prokaryotic host cell, (2) a DNA sequence that encodes a DNA-binding domain and that is functionally associated with the transcriptional and translational elements of the first gene, and (3) a means for inserting a DNA sequence encoding a first test polypeptide into the first vector in such a manner that the first test polypeptide is capable of being expressed in-frame as part of a bait fusion protein containing the DNA binding domain. The kit will also include a second vector for encoding a second fusion protein ("prey fusion protein"), which comprises a second gene including (1) transcriptional and translational elements that direct expression in a prokaryotic host cell, (2) a DNA sequence that encodes an activation tag, such as a polymerase interaction domain (PID), the activation tag DNA sequence being functionally associated with the transcriptional and translational elements of the second gene, and (3) a means for inserting a DNA sequence encoding the second test polypeptide into the second vector in such a manner that the second test polypeptide is capable of being expressed in-frame as part of a prey fusion protein containing the activation tag. Additionally, the kit will include a prokaryotic host cell containing a reporter gene having a binding site ("DBD recognition element") for the DNA-binding domain, wherein the reporter gene expresses a detectable protein when a prey fusion protein interacts with a bait fusion protein bound to the DBD recognition element. Preferably, the host cell by itself does not express a protein having the function of the reporter gene product, a protein which binds the DBD recognition element and competes with the DBD, and/or otherwise activates expression of the reporter gene. Binding of the bait and prey fusion proteins in the host cell results in measurable change in expression of the reporter gene, e.g., relative to the absence of an interaction between the two fusion proteins.

Other features and advantages of the invention will be apparent from the following detailed description, and from the claims. The practice of the present invention will employ, unless otherwise indicated, conventional techniques of cell biology, cell culture, molecular biology, transgenic biology, microbiology, recombinant DNA, and immunology, which are within the skill of the art. Such techniques are explained fully in the literature. See, for example, *Molecular Cloning A Laboratory Manual,* 2nd Ed., ed. by Sambrook, Fritsch and Maniatis (Cold Spring Harbor Laboratory Press: 1989); *DNA Cloning,* Volumes I and II (D. N. Glover ed., 1985); *Oligonzicleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., New York); *Gene Transfer Vectors For Mammalian Cells* (J. H. Miller and M. P. Calos eds., 1987, Cold Spring Harbor Laboratory); *Methods In Enzymology,* Vols. 154 and 155 (Wu et al. eds.), *Immunochemical Methods In Cell And Molecular Biology* (Mayer and Walker, eds., Academic Press, London, 1987); *Handbook Of Experimental Immunology,* Volumes I–IV (D. M. Weir and C. C. Blackwell, eds., 1986); *Manipulating the Mouse Embryo,* (Cold Spring Harbor Laboratory Press, Cold Spring Harbor, N.Y., 1986).

BRIEF DESCRIPTION OF THE FIGURES

FIG. 1A illustrates that λcI binds DNA as a dimer, and pairs of dimers bind cooperatively to adjacent operator sites.

FIG. 1B illustrates the transcriptional complexes which may be formed with a prey fusion protein resulting from replacement of the α-CTD (C-terminal domain) with the λcI-CTD. As described in the appended examples, the hybrid a gene was generated by replacing the gene segment encoding the α-CTD with a gene segment encoding the λcI-CTD. A derivative of the lac promoter was also created bearing a single λ operator ($O_R2$) in place of the CRP-binding site (centered 62 bps upstream of the transcription startpoint).

DETAILED DESCRIPTION OF THE INVENTION

Figure 2A:
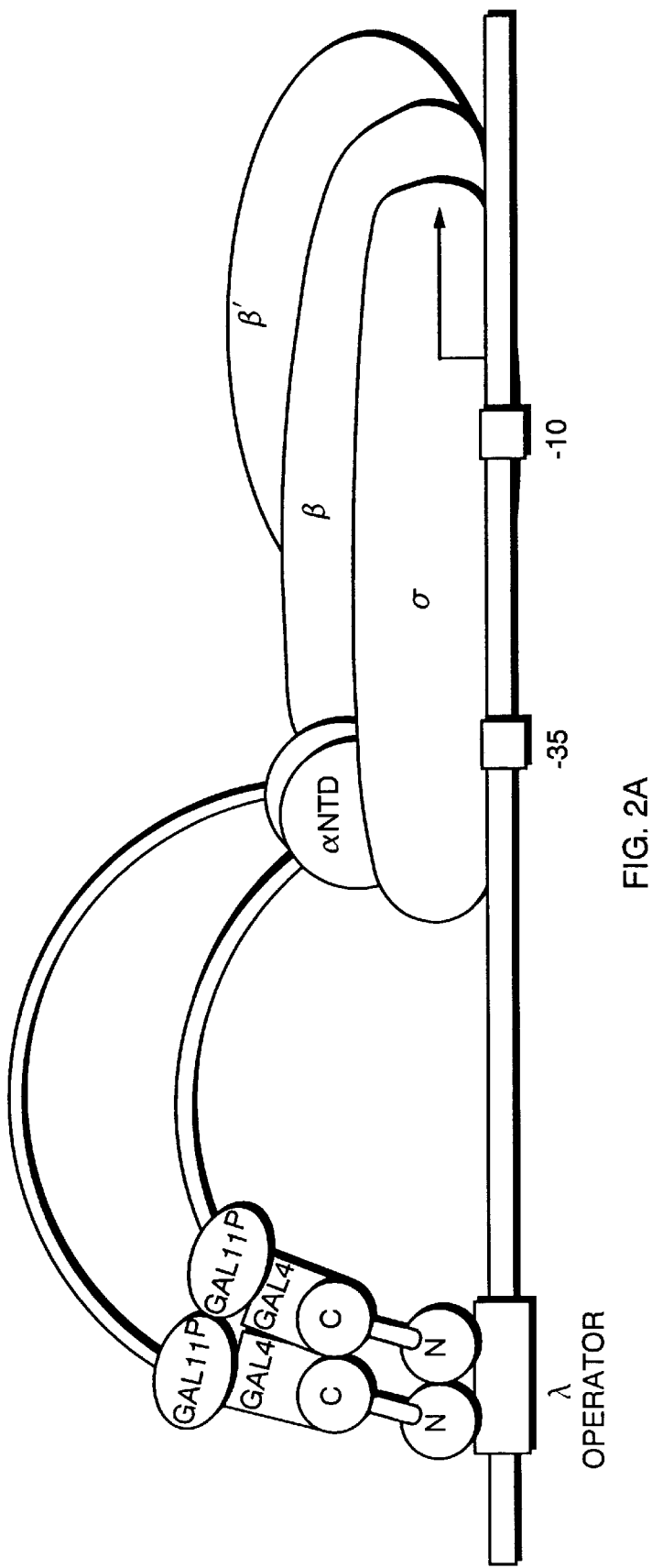
FIG. 2A illustrates the transcriptional complexes which may be formed with a prey fusion protein resulting from replacement of the α-CTD with a portion of the $GAL11^P$ protein and a bait protein comprised of the λcI protein having a portion of the GAL4 protein fused at its C-terminus.

The eukaryotic interaction trap system ("ITS"), originally developed by Fields and Song (*Nature* (1989) 340:245) in yeast, is a powerful in vivo assay to detect protein-protein interactions. It has already had a large impact on basic and applied biological research. In industry, it is being used to isolate and characterize new targets for drug development. It permits researchers to isolate small organic molecules, peptides, and nucleic acids that may lead to new drugs. Future applications for genome characterization and for modulation of specific protein-protein interactions are on the horizon. The ramifications of this technology promise to be exciting. In this system, one protein is fused to a DNA binding domain, while the other is fused to a transcriptional activation domain. If the two proteins interact in a yeast cell, a functional transcriptional activator is reconstituted, the activity of which is monitored by the expression of a reporter gene containing a cognate site for the DNA binding domain. A number of different DNA binding domains and activation domains have been successfully used in this system, as well as a variety of different reporter genes. However, the interaction trap assays described in the art have only been generated in eukaryotic cells. There are no examples in the art of an analogous system being generated in prokaryotes.

The present invention makes available an interaction trap system (hereinafter "ITS") which is derived using recombinantly engineered prokaryotic cells. As described in the appended examples, the prokaryotic ITS derives in part from the unexpected finding that the natural interaction between a transcriptional activator and subunit(s) of an RNA polymerase complex can be replaced by heterologous protein-protein interactions which are capable of activating transcription. The versatility of the prokaryotic ITS makes it generally suitable for many, if not all of the applications of the eukaryotic ITS. Moreover, the ease of manipulation of the bacterial cells, e.g., in transformation or transfection and culturing, means that even larger polypeptide libraries can be screened in the prokaryotic ITS.

The prokaryotic interaction trap systems described herein provide advantages over the conventional eukaryotic ITS methods. For example, the use of bacterial host cells to generate an interaction trap system provides a system which is generally easier to manipulate genetically relative to the eukaryotic systems. Furthermore, bacterial host cells are easier to propagate. The shorter doubling times for bacteria will often provide for development of a signal in the ITS in a shorter time period than would be obtained with a eukaryotic ITS. Another advantage which may be realized in the practice of the present invention is that detection of reporter gene expression can, in certain embodiments, be technically easier relative to the eukaryotic system. The expression of a βμ-galactosidase reporter gene, for example, is more easily detected in bacteria than in yeast.

Yet another benefit which may be realized by the use of the prokaryotic ITS is lower spurious activation relative to, e.g., the ITS fusion proteins employed in yeast. In eukaryotic cells, spurious transcription activation by a bait polypeptide having a high acidic residue content can be problematic. This is not expected to be an impediment for the use of such bait polypeptides in the prokaryotic ITS.

Another benefit in the use of the prokaryotic ITS is that, in contrast to the eukaryotic system, nuclear localization of the bait and prey polypeptides is not a concern in bacterial cells.

Still another advantage of the use of the prokaryotic ITS can be realized where the bait and/or prey polypeptides are derived from eukaryotic sources, such as human. One problem that can occur when using the yeast ITS of the prior art is that mammalian/eukaryotic derived bait or prey may retain sufficient biological activity in yeast cells so as to confound the results of the ITS. The greater evolutionary divergence between eukaryotes and bacteria reduces the likelihood of a similar problem in the prokaryotic ITS of the present invention.

I. Overview

A method and reagents for detecting interactions between two polypeptides is provided in accordance with the present invention. The method generally includes, with some variations, providing a recombinant prokaryotic cell engineered to include a reporter gene construct including (i) a binding site ("DBD recognition element") for a DNA-binding domain operably linked to (ii) at least one reporter gene which expresses a reporter gene product when the gene is transcriptionally activated.

The cell is also engineered to include a first chimeric gene which is capable of being expressed in the host cell. The chimeric gene encodes a fusion protein (a "bait" fusion protein) which comprises (i) a DNA-binding domain that specifically binds the recognition element on the reporter gene in the host cell, and (ii) a "bait" polypeptide, e.g., a test polypeptide for which complex formation is to be tested. The DNA-binding domain and bait polypeptide are preferably from heterologous sources.

A second chimeric gene is also provided in the cell, the second chimeric gene encoding a second hybrid protein (a "prey" fusion protein) comprising an "activation tag", e.g., a polypeptide capable of recruiting an active polymerase complex, fused to a test polypeptide sequence (a "prey" polypeptide) which is to be tested for interaction with the bait polypeptide. In certain embodiments of the prokaryotic ITS, the activation tag can be a polymerase interaction domain. For instance, the polymerase interaction domain ("PID") can include determinants of an RNA polymerase subunit that mediate its interaction with other polymerase subunits, thus enabling the prey fusion protein to be assembled into a functional polymerase enzyme.

In other embodiments, the polymerase interaction domain can be a polypeptide sequence which interacts with, or is covalently bound to, one or more subunits (or a fragment thereof) of an RNA polymerase complex in order to recruit functional polymerases to the DNA bound prey fusion protein. Such polypeptide sequences can be derived from, e.g., transcription factors or auxiliary proteins of polymerase complexes or even from random polypeptide libraries (e.g., not occurring naturally). For instance, the prey fusion protein can be derived with an activation domain of a transcriptional activator, rather than with the polymerase interaction domain described above. In those embodiments, the prey fusion protein must function to directly or indirectly recruit the RNA polymerase enzyme to the reporter gene by forming bridging contacts to one or more of the polymerase subunits. In either embodiment, expression of the reporter gene occurs when the activation tag is brought into sufficient proximity to the reporter gene by the prey protein contacting a bait protein whose DNA-binding domain is bound to the recognition element.

In one embodiment, both the first and the second chimeric genes are introduced into the host cell on plasmids.

The bait/prey-mediated interaction, if any, between the first and second fusion proteins in the host cell causes an RNA polymerase complex to be recruited to the transcriptional regulatory sequences of the reporter gene with concomitant transcription of the reporter gene. The method is carried out by introducing the first and second chimeric genes into the host cell, and subjecting that cell to conditions under which the first and second hybrid proteins are expressed in sufficient quantity for expression of the reporter gene to be activated by interaction of the two fusion proteins if that interaction occurs. The formation of a complex between the bait and prey fusion proteins results in a detectable signal produced by a change in the expression level of the reporter gene. Accordingly, the formation of a complex between a sample target protein and proteins encoded by a cDNA library, for example, can be detected, and ITS cells isolated, if desired, on the basis of evaluating the level of expression of the reporter gene.

The method of the present invention, as described above, may be practiced using a kit for detecting interaction between a first test protein and a second test protein. The kit typically will include the two vectors for generating the chimeric proteins, a reporter gene construct, and a host cell. In certain embodiments, any and all of the expression vectors and reporter gene construct can be integrated into the genome of the host cell. The first vector contains a promoter and other relevant transcription and/or translation sequences to direct expression of the first chimeric gene. The first chimeric gene includes a DNA sequence that encodes a DNA-binding domain and a (unique) restriction site(s) for inserting a DNA sequence encoding a first test polypeptide in such a manner that the first test protein is expressed as part of a hybrid protein with the DNA-binding domain. The first vector also includes a means for replicating itself in the host cell. Also included on the first vector is, preferably, a first marker gene, the expression of which in the host cell permits selection of cells containing the first marker gene. Exemplary marker genes confer antibiotic resistance. Preferably, the first vector is a plasmid.

The second vector is derived for generating the second chimeric protein. The second chimeric gene includes a promoter and other relevant transcription and/or translation sequences to direct expression of the chimeric gene. The second chimeric gene also includes a DNA sequence that encodes an activation tag and a (unique) restriction site(s) to insert a DNA sequence encoding the second test polypeptide into the vector, in such a manner that the second test protein is capable of being expressed as part of a hybrid protein with the activation tag. The second vector further includes a means for replicating itself in the host cell. The second vector also includes a second marker gene, the expression of which in the host cell permits selection of cells containing the second marker gene.

The kit includes a prokaryotic host cell, preferably a strain of E. coli or other suitable bacterial strain, which can be engineered to express the bait and prey fusion proteins, and express the reporter gene in a manner dependent on the formation of complexes including the two fusion proteins. The host cell contains the reporter gene having a DNA binding site for the DNA-binding domain of the first hybrid protein. The binding site is positioned so that, upon interaction of the bait and prey fusion proteins, an RNA polymerase complex is recruited to the promoter sequence of the reporter gene, causing expression of the reporter gene. The host cell, by itself, is preferably incapable of expressing a protein having a function of the first marker gene, the second marker gene, the reporter gene, or a protein which activates the reporter gene.

Accordingly, in using the kit the interaction of the bait and prey components of the two fusion proteins in the host cell causes a measurable change in expression of the reporter gene relative to the case where one or both of the DBD and activation tag are provided alone, or alternatively the test polypeptides do not interact. The reporter gene may encode an enzyme or other product that can be readily measured. Such measurable activity may include the ability of the cell to grow only when the reporter gene is transcribed, or the presence of detectable enzyme activity only when the reporter gene is transcribed.

The cells containing the two hybrid proteins are incubated in/on an appropriate medium and the cells are monitored, and optionally selected, by detecting expression of the reporter gene product. Expression of the reporter gene is an indication that the bait protein and the prey protein have interacted.

II. Definitions

Before further description of the invention, certain terms employed in the specification, examples and appended claims are, for convenience, collected here.

The term "prokaryote" is art recognized and refers to a unicellular organism lacking a true nucleus and nuclear membrane, having genetic material composed of a single covalent closed circle of double-stranded DNA. Prokaryotes with the exception of mycoplasmas have a rigid cell wall. In some systems of classification, a division of the kingdom Prokaryotae, Bacteria include all prokaryotic organisms that are not blue-green algae (Cyanophyceae). In other systems, prokaryotic organisms without a true cell wall are considered to be unrelated to the Bacteria and are placed in a separate class—the Mollicutes.

The term "bacteria" is art recognized and refers to certain single-celled microorganisms of about 1 micrometer in diameter; most species have a rigid cell wall. They differ from other organisms (eukaryotes) in lacking a nucleus and membrane-bound organelles and also in much of their biochemistry.

As used herein, "recombinant cells" include any cells that have been modified by the introduction of heterologous DNA.

As used herein, the terms "heterologous DNA" or "heterologous nucleic acid" is meant to include DNA that does not occur naturally as part of the genome in which it is present, or DNA which is found in a location or locations in the genome that differs from that in which it occurs in nature, or occurs extra-chromasomally, e.g., as part of a plasmid.

By "protein" or "polypeptide" is meant a sequence of amino acids of any length, constituting all or a part of a non-natural occurring polypeptide or peptide, or constituting a non-naturally-occurring polypeptide or peptide (e.g., a randomly generated peptide sequence or one of an intentionally designed collection of peptide sequences).

By a "DNA binding domain" or "DBD" is meant a polypeptide sequence which is capable of directing specific polypeptide binding to a particular DNA sequence (i.e., to a DBD recognition element). The term "domain" in this context is not intended to be limited to a discrete folding domain. Rather, consideration of a polypeptide as a DBD for use in the bait fusion protein can be made simply by the observation that the polypeptide has a specific DNA binding activity. DNA binding domains, like activation tags, can be derived from proteins ranging from naturally occurring proteins to completely artificial sequences.

The term "activation tag" refers to a polypeptide sequence which participates as a component of an RNA polymerase, or which recruits an active polymerase complex. For instance, in the prokaryotic ITS the activation tag can be a polymerase interaction domain or some other polypeptide sequence which interacts with, or is covalently bound to, one or more subunits (or a fragment thereof) of an RNA polymerase complex. Activation tags can also be sequences which are derived from, e.g., transcription factors or other proteins which interact with, directly or indirectly, wit polymerase complexes. Activation tags can even be from random polypeptide libraries.

The term "polymerase interaction domain" or "PID" refers to a polypeptide seqence which includes determinants of an RNA polymerase subunit that mediate its interaction with other polymerase subunits, or a polypeptide sequence which interacts with, or is covalently bound to, one or more subunits (or a fragment thereof) of an RNA polymerase complex.

The terms "recombinant protein", "heterologous protein" and "exogenous protein" are used interchangeably throughout the specification and refer to a polypeptide which is produced by recombinant DNA techniques, wherein generally, DNA encoding the polypeptide is inserted into a suitable expression vector which is in turn used to transform a host cell to produce the heterologous protein. That is, the polypeptide is expressed from a heterologous nucleic acid.

As used herein, a "reporter gene construct" is a nucleic acid that includes a "reporter gene" operably linked to transcriptional regulatory sequences. Transcription of the reporter gene is controlled by these sequences. The ability of at least one or more of these control sequences to direct transcription of the reporter gene is directly or indirectly dependent on a transcriptional complex recruited by virtue of interaction between the bait and prey fusion proteins. The transcriptional regulatory sequences can include a promoter and other regulatory regions that modulate the activity of the promoter, or regulatory sequences that modulate the activity or efficiency of the RNA polymerase that recognizes the promoter. Such sequences are herein collectively referred to as transcriptional regulatory elements or sequences. The reporter gene construct will also include a "DBD recognition element" which is a nucleotide sequence that is specifically bound by the DNA binding domain of the bait fusion protein. The DBD recognition element is located sufficiently proximal to the promoter sequence of the reporter gene so as to cause increased reporter gene expression upon recruitment of an RNA polymerase complex by a bait fusion protein bound at the recognition element.

As used herein, a "reporter gene" is a gene whose expression may be assayed; reporter genes may encode any protein that provides a phenotypic marker, for example: a protein that is necessary for cell growth or a toxic protein leading to cell death, e.g., a protein which confers antibiotic resistance or complements an auxotrophic phenotype; a protein detectable by a colorimetric/fluorometric assay leading to the presence or absence of color/fluorescence; or a protein providing a surface antigen for which specific antibodies/ligands are available.

By "operably linked" is meant that a gene and transcriptional regulatory sequence(s) are connected in such a way as to permit expression of the gene in a manner dependent upon factors interacting with the regulatory sequence(s). In the case of the reporter gene, the DBD recognition element will also be operably linked to the reporter gene such that transcription of the reporter gene will be dependent, at least in part, upon bait-prey complexes bound to the recognition element.

By "covalently bonded" it is meant that two domains are joined by covalent bonds, directly or indirectly. That is, the "covalently bonded" proteins or protein moieties may be immediately contiguous or may be separated by stretches of one or more amino acids within the same fusion protein.

By "altering the expression of the reporter gene" is meant a statistically significant increase or decrease in the expression of the reporter gene to the extent required for detection of a change in the assay being employed. It will be appreciated that the degree of change will vary depending upon the type of reporter gene construct or reporter gene expression assay being employed.

The terms "interactors", "interacting proteins" and "candidate interactors" are used interchangeably herein and refer to a set of proteins which are able to form complexes with one another, preferably via non-covalent interactions.

By "test protein" or "test polypeptide" is meant all or a portion of one of a pair of interacting proteins provided as part of the bait or prey fusion proteins.

By "randomly generated" is meant sequences having limited or no predetermined sequence; this is contrasted with "intentionally designed" sequences which have a DNA or protein sequence or motif determined prior to their synthesis.

By "amplification" or "clonal amplification" is meant a process whereby the density of host cells having a given phenotype is increased.

The terms "pool" of polypeptides, "polypeptide library" or "combinatorial polypeptide library" are used interchangeably herein to indicate a variegated ensemble of polypeptide sequences, where the diversity of the library may result from cloning, mutagenesis, or random or semi-random synthesis of nucleic acid sequences. The terms "pool" of genes, "gene library" or "combinatorial gene library" have a similar meaning, indicating a variegated ensemble of nucleic acids.

By "screening" is meant a process whereby a gene library is surveyed to determine whether there exists within this population one or more genes which encode a polypeptide having a particular binding characteristic in the interaction trap assay.

It is further noted that the following description of particular arrangements of test polypeptide sequences in terms of being part of the bait or prey fusion proteins is, in general, arbitrary. As will be apparent from the description, the test polypeptide portions of any given pair of interacting bait and prey fusion proteins may ordinarily be swapped with each other.

Each component of the system is now described in more detail.

III. Bait protein constructs

One of the first steps in the use of the interaction trap system of the present invention is to construct the bait fusion protein. To do this, sequences encoding a protein of interest or a polypeptide library are cloned in-frame to a sequence encoding a DNA binding domain (DBD), e.g., a polypeptide which specifically binds to a defined nucleotide sequence. Those skilled in the art will appreciate from the present disclosure that there are a wide variety of DNA binding domains that can be used to construct the bait fusion protein, including polypeptides derived from naturally occurring DNA binding proteins, as well as polypeptides derived from proteins artificially engineered to interact with specific DNA sequences. Basic requirements for the bait fusion protein include the ability to specifically bind a defined nucleotide sequence, and (preferably) that the bait fusion protein cause little or no transcriptional activation of the reporter gene in the absence of an interacting prey fusion protein. In addition, the bait polypeptide sequence should not affect the ability of the DBD to bind to its cognate sequence in the transcriptional regulatory element of the reporter gene.

In one preferred embodiment, the DBD portion of the bait fusion protein is derived using all, or a DNA binding portion of a transcriptional regulatory protein, e.g., of either a transcriptional activator or transcriptional repressor, which retains the ability to selectively bind to particular nucleotide sequences. The DNA binding domains of the bacteriophage λcI protein (hereinafter "λcI") and the $E.\ coli$ LexA repressor (hereinafter "LexA") represent preferred DNA binding domains for the bait fusion proteins of the instant interaction trap system. The use of a well-defined system, such as λcI or LexA, allows knowledge regarding the interaction between a DNA binding domain and its DBD recognition element (i.e., the λcI or LexA operator) to be exploited for the purpose of optimizing operator occupancy and/or optimizing the geometry of the bound bait protein to effect maximal gene activation. In constructing the bait fusion protein, the DNA binding activity of the fusion protein can be, as appropriate, provided by using all or a portion of the transcriptional regulatory protein. Depending on the sequences of the regulatory protein retained in the bait fusion protein, it may be desirable to mutate certain residues of those retained sequences which may contribute to transcriptional activation or repression in the absence of the prey fusion protein, e.g., in order to reduce prey-independent modulation of reporter gene transcription.

However, any other transcriptionally inert or essentially transcriptionally-inert DNA binding domain may be used to create the bait fusion protein in the instant interaction trap system; such DNA binding domains are well known and include, but are not limited to such motifs as helix-turn-helix motifs (such as found in λcI), winged helix-turn helix motifs (such as found in certain heat shock transcription factors), and/or zinc fingers/zinc clusters. As merely illustrative, the bait fusion protein can be constructed utilizing the DNA binding portions of the LysR family of transcriptional regulators, e.g., Trp1, HvY, OccR, OxyR, CatR, NahR, MetR, CysB, NodD or SyrM (Schell et al. (1993) $Annu\ Rev\ Microbiol$ 47:597), or the DNA binding portions of the PhoB/OmpR-related proteins, e.g., PhoB, OmpR, CacC, PhoM, PhoP, ToxR, VirG or SfrA (Makino et al. (1996) $J.\ Mol\ Biol$ 259:15), or the DNA binding portions of histones H1 or H5 (Suzuki et al. (1995) $FEBS\ Lett$ 372:215). Other exemplary DBD's which can be used to generate the bait fusion protein include DNA binding portions of the P22 Arc repressor, MetJ, CENP-B, Rap1, Xy1S/Ada/AraC, Bir5 or DtxR.

Furthermore, the DNA binding domain need not be obtained from the protein of a prokaryote. For example, polypeptides with DNA binding activity can be derived from proteins of eukaryotic origin, including from yeast. For example, the DBD portion of the bait fusion protein can include polypeptide sequences from such eukaryotic DNA binding proteins as p53, Jun, Fos, GCN4, or GAL4. Likewise, the DNA binding portion of the bait fusion protein can be generated from viral proteins, such as the pappillomavirus E2 protein (c.f., PCT publication WO 96/19566). In yet other embodiments, the DNA binding protein can be generated by combinatorial mutagenic techniques, and represent a DBD not naturally occurring in any organism. A variety of techniques have been described in the art for generating novel DNA binding proteins which can selectively bind to a specific DNA sequence (c.f., U.S. Pat. No. 5,198,346 entitled "$Generation\ and\ selection\ of\ novel\ DNA\text{-}binding\ proteins\ and\ polypeptides$").

As appropriate, the DNA binding motif used to generate the bait fusion protein can include oligomerization motifs. As known in the art, certain transcriptional regulators dimerize, with dimerization promoting cooperative binding of the two monomers to their cognate recognition elements. For example, where the bait protein includes a LexA DNA binding domain, it can further include a LexA dimerization domain; this optional domain facilitates efficient LexA dimer formation. Because LexA binds its DNA binding site as a dimer, inclusion of this domain in the bait protein also optimizes the efficiency of operator occupancy (Golemis and Brent, (1992) *Mol. Cell Biol.* 12:3006). Other oligomerization motifs useful in the present invention will be readily recognized by those skilled in the art. Exemplary motifs include the oligomerization domain of λcI, the tetramerization domain of p53 and the tetramerization domain of BCR-ABL. In addition, the art also provides a variety of techniques for identifying other naturally occurring oligomerization domains, as well as oligomerization domains derived from mutant or otherwise artificial sequences. See, for example, Zeng et al. (1997) *Gene* 185:245.

As described below, binding efficiency of the bait fusion protein for the recognition element of the reporter gene can also be fine tuned by the particular sequence of the DBD recognition element, and its proximity to other transcriptional regulatory sequences in the reporter gene construct. Likewise, the binding efficiency and/or specificity of the DBD portion of the bait fusion protein can be altered by mutagenesis.

The bait portion of the bait fusion protein may be chosen from any protein of interest and includes proteins of unknown, known, or suspected diagnostic, therapeutic, or pharmacological importance. Exemplary bait proteins include, but are not limited to, oncoproteins (such as Myc, particularly the C-terminus of Myc, Ras, Src, Fos, and particularly the oligomeric interaction domains of Fos), tumor-suppressor proteins (such as p53, Rb, INK4 proteins [p16INK4a, p15INK4b], CIP/KIP proteins [p21CIP1, p27KIP1]) or any other proteins involved in cell-cycle regulation (such as kinases and phosphatases). In other embodiments, the bait polypeptide can be generated using all or a portion of a protein involved in signal transduction, including such motifs as SH2 and SH3 domains, ITAMs, ITIMs, kinase, phospholipase, or phosphatase domains, cytoplasmic tails of receptors and the like. Yet other preferred bait fusion proteins are generated with cytoskeletal proteins or factors involved in transcription or translation, or portions thereof. Still other bait fusion proteins can be generated with viral proteins.

In preferred embodiments, where the bait protein includes a catalytic domain of an enzyme, the fusion protein is derived with a catalytically inactive mutant, most preferably a mutant which binds substrate with about the $K_m$ of the wild-type enzyme but with a greatly diminished $K_{cat}$ for the catalyzed reaction with the substrate. For example, mutation of a residue in the catalytic site of the enzyme can give rise to such catalytically inactive mutants. Particular examples include point mutation of the active site lysine of a kinase, the active site serine of a serine protease or the active site cysteine of a phosphatase. Thus, the binding of the bait polypeptide portion of the fusion protein to a polypeptide substrate presented by a prey fusion protein can be enhanced. In each case, the protein of interest is fused to a DNA binding domain as generally described herein.

The use of recombinant DNA techniques to create a fusion gene, with the translational product being the desired bait fusion protein, is well known in the art. Essentially, the joining of various DNA fragments coding for different polypeptide sequences is performed in accordance with conventional techniques, employing blunt-ended or stagger-ended termini for ligation, restriction enzyme digestion to provide for appropriate termini, filling in of cohesive ends as appropriate, alkaline phosphatase treatment to avoid undesirable joining, and enzymatic ligation. Alternatively, the fusion gene can be synthesized by conventional techniques including automated DNA synthesizers. In another method, PCR amplification of gene fragments can be carried out using anchor primers which give rise to complementary overhangs between two consecutive gene fragments which can subsequently be annealed to generate a chimeric gene sequence (see, for example, *Current Protocols in Molecular Biology*, Eds. Ausubel et al. John Wiley & Sons: 1992).

It may be necessary in some instances to introduce an unstructured polypeptide linker region between the DNA binding domain of the fusion protein and the bait polypeptide sequence. Where the bait fusion protein also includes oligomerization sequences, it may be preferable to situate the linker between the oligomerization sequences and the bait polypeptide. The linker can facilitate enhanced flexibility of the fusion protein allowing the DBD to freely interact with a responsive element, and, if present, the oligomerization sequences to make inter-protein contacts. The linker can also reduce steric hindrance between the two fragments, and allow appropriate interaction of the bait polypeptide portion with a prey polypeptide component of the interaction trap system. The linker can also facilitate the appropriate folding of each fragment to occur. The linker can be of natural origin, such as a sequence determined to exist in random coil between two domains of a protein. An exemplary linker sequence is the linker found between the C-terminal and N-terminal domains of the RNA polymerase α subunit. Other examples of naturally occurring linkers include linkers found in the λcI and LexA proteins. Alternatively, the linker can be of synthetic origin. For instance, the sequence $(Gly_4Ser)_3$ can be used as a synthetic unstructured linker. Linkers of this type are described in Huston et al. (1988) *PNAS* 85:4879; and U.S. Pat. No. 5,091,513, both incorporated by reference herein. Another exemplary embodiment includes a poly alanine sequence, e.g., $(Ala)_3$.

As set out above, the bait fusion protein should have little to no transcriptional activation ability by itself. In a preferred embodiment, a repression assay is carried out as a control to confirm that lack of transcriptional activation by the bait fusion protein is not simply because the fusion protein is mis-folded, or is sequestered in inclusion bodies. In one embodiment, the repression assay tests the ability of the fusion protein to competitively block transcription of a reporter gene construct containing a DBD recognition element. In such a repression assay, the DBD recognition element is positioned in such a way that binding of a protein to the recognition element inhibits transcription, e.g., the recognition element is placed between the −10 and −35 region of the promoter. Where the bait fusion protein includes the DNA binding domain of λcI, the ability of the fusion protein to bind to a λ operator sequence (e.g., which could serve as the DBD recognition element) can be validated by its ability to confer on an *E. coli* strain immunity to infection by λ phage.

IV. Prey protein constructs

In preferred embodiments, the prey fusion protein comprises: (1) a target polypeptide sequence, capable of forming an intermolecular association with the bait polypeptide which is to be tested for such binding activity, and (2) an activation tag such as a PID. As described herein, the activation tag can be, for example, all or a portion of an RNA polymerase subunit, such as the polymerase interaction domain of the N-terminal domain (α-NTD) of the RNA polymerase α subunit. As described above, protein-protein contact between the bait and prey fusion proteins (via the interacting bait and prey polypeptide portions of those proteins) links the DNA-binding domain of the bait fusion protein with the polymerase interaction domain of the prey fusion protein, generating a protein complex capable of directly recruiting a functional RNA polymerase enzyme to DNA sequences proximate to the DNA bound bait protein, i.e., to the reporter gene.

DNA dependent RNA polymerase in $E.$ $coli$ and other bacteria consists of an enzymatic core composed of subunits $\alpha$, $\beta$, and $\beta'$ in the stoichiometry $\alpha_2\beta\beta'$, and one of several alternative a factors responsible for specific promoter recognition. In one embodiment, the prey fusion protein includes a sufficient portion of the amino-terminal domain of the a subunit to permit assembly of transcriptionally active RNA polymerase complexes which include the prey fusion protein. The $\alpha$ subunit, which initiates the assembly of RNA polymerase by forming a dimer, has two independently folded domains (Ebright et al. (1995) $Curr$ $Opin$ $Genet$ $Dev$ 5:197). The larger amino-terminal domain ($\alpha$-NTD) mediates dimerization and the subsequent assembly of the polymerase complex. The prey polypeptide can be fused in frame to the $\alpha$-NTD (see appended examples) or a fragment thereof which retains the ability to assemble a functional RNA polymerase complex.

Figure 2B:
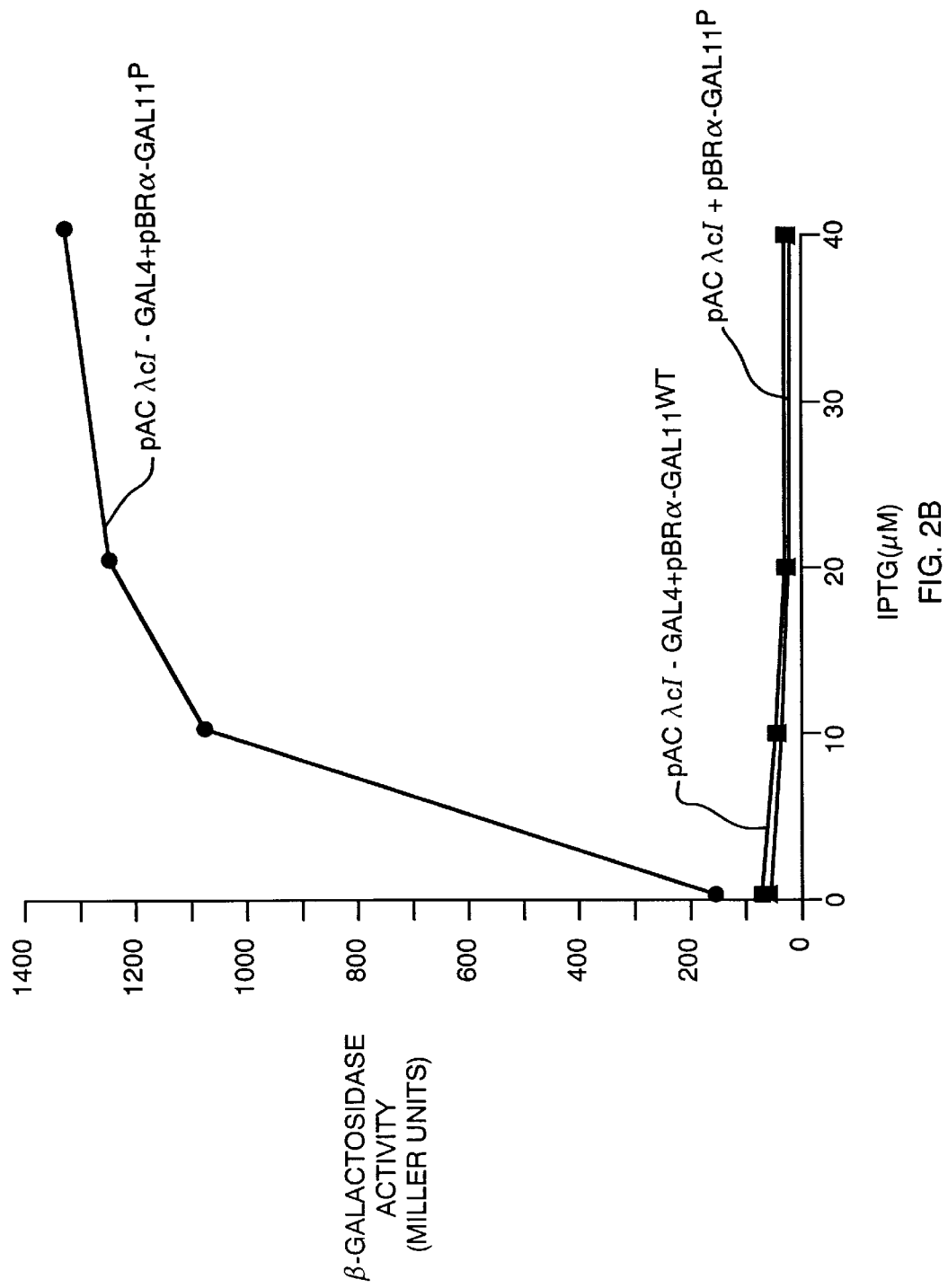
FIG. 2B is a graph indicating the abilities of various fusion proteins of GAL4, GAL11, and $GAL11^P$ to function in the subject ITS.

To further illustrate the ability of the $\alpha$ subunit to be utilized in the subject ITS, the coding sequence for $\alpha$-NTD was fused to the coding sequence for a portion of the yeast protein GAL11$^P$, a mutant form of GAL11. See FIG. 2A and Himmelfarb et al. (1990) $Cell$ 63:1299–309. The "P" mutation confers upon GAL11, a component of the RNA polymerase II holoenzyme in yeast, the ability to interact with the dimerization region of GAL4. We also constructed a fusion protein comprised of the $\lambda$cI protein having the dimerization region of GAL4 fused at its C-terminus. As demonstrated in FIG. 2B, the co-expression of both fusion proteins can activate the expression of a reporter gene under the transcriptional control of a $\lambda$cI operator. Substitution of the wildtype GAL11 sequence for the GAL11$^P$ sequence results in loss of transcriptional activity of the co-expressed fusion proteins.

Figure 4:
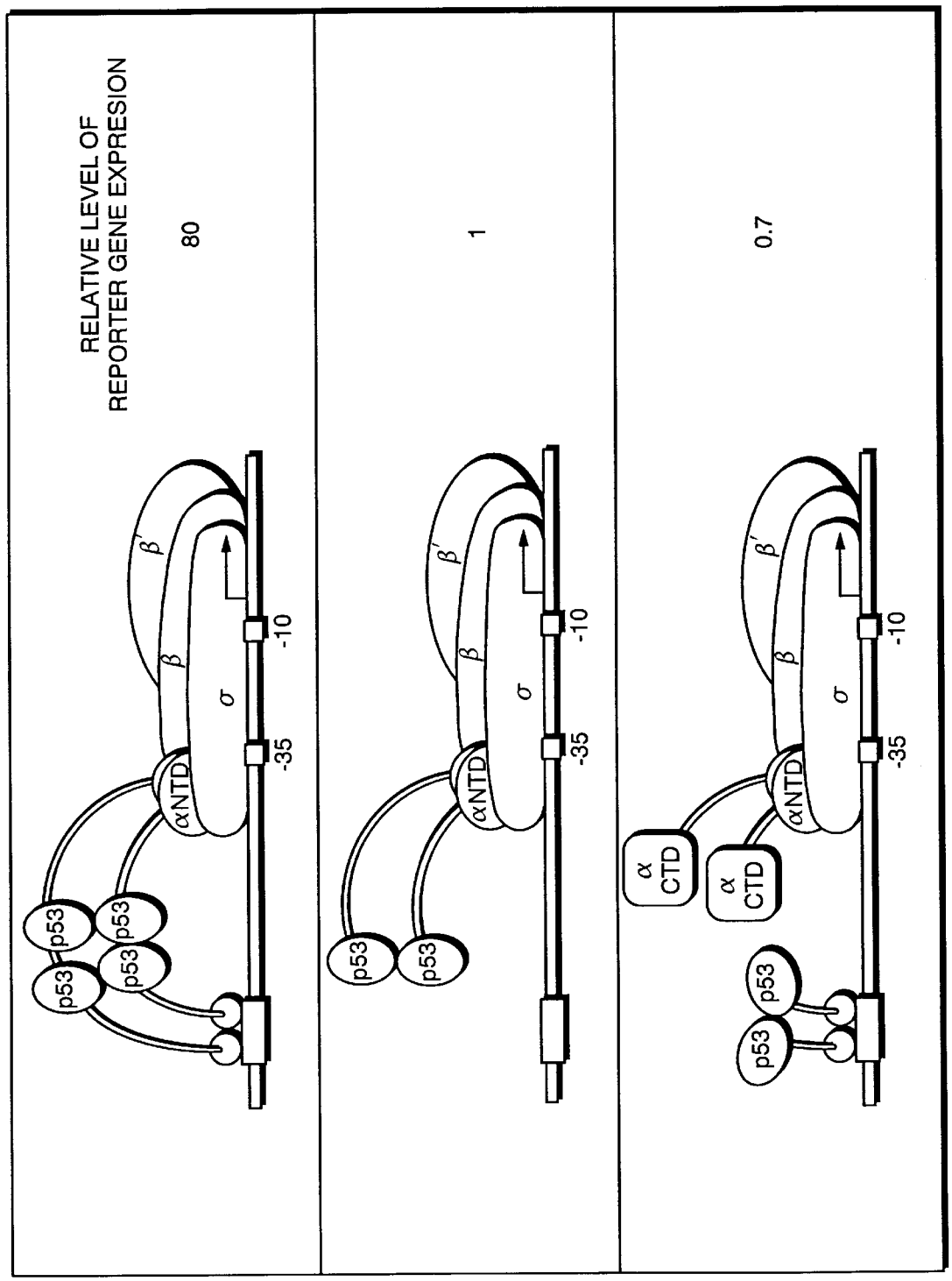
FIG. 4 is a table illustrating the relative level of reporter gene expression with various combinations of prey and bait fusion proteins containing a p53 tetramerization domain.

FIG. 4 similarly illustrates the use of the $\alpha$-NTD. In that embodiment, the tetramerization domain of p53 was fused to both $\alpha$-NTD and to the DBD of $\lambda$cI. As demonstrated in FIG. 4, the co-expression of both fusion proteins can activate the expression of a reporter gene under the transcriptional control of a $\lambda$cI operator, presumably by p53-mediated tetramerization. Expression of only the $\lambda$cI-p53 fusion protein, e.g., in the presence of the wildtype a subunit, did not activate expression of the reporter gene above basal levels.

The present invention also contemplates the use of polymerase interaction domains containing portions of other RNA polymerase subunits or portions of molecules which associate with an RNA polymerase subunit or subunits. Contemporary models of the polymerase complex predict a substantial degree of intramolecular motion within the transcription complex. Movement of parts of the enzyme complex relative to each other is believed to be realized by structurally independent domains, such as the N-terminal and C-terminal domains of the a subunit described above. Accordingly, it is possible that the paradigm of transcriptional activation realized with fusion proteins incorporating only a portion of the a subunit is also applicable to fusion proteins generated with portions of other polymerase subunits, preferably subunits which are an integral part of or tightly associated with the polymerase complex, e.g., such as the $\beta$, $\beta'$, $\omega$ and/or $\sigma$ subunits. The use of portions of such other subunits to generate a prey fusion protein are, like the $\alpha$-NTD example above, expected to provide fusion proteins which retain the ability to form active polymerase complexes. For example, Severinov et al. (1995) $PNAS$ 92:4591 describes the ability of fragments of the $\beta$ subunit (encoded by the $E.$ $coli$ rpoB gene) to reconstitute a functional polymerase enzyme. It is noted that it may be a requirement of embodiments utilizing prey fusion proteins including PIDS of the $\beta$, $\beta'$ or $\sigma$ subunits that other fragments of the subunit be provided, e.g., co-expressed, in the host cell.

Figure 3A:
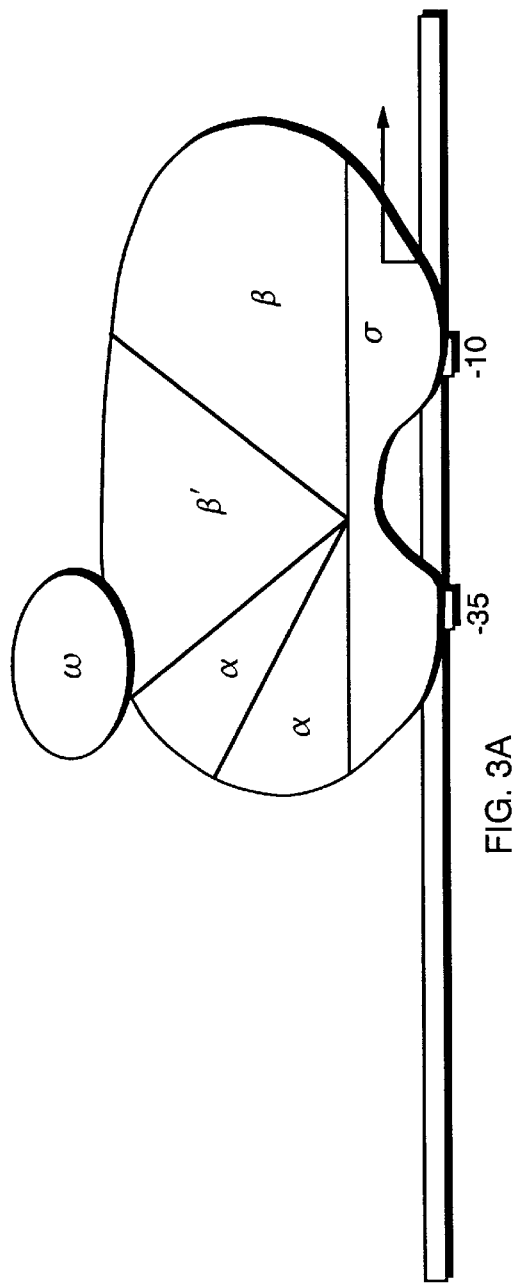
FIG. 3A depicts the presence of the ω subunit in *E. coli* RNA polymerase complexes.

To further illustrate such equivalents, it is noted that highly purified $E.$ $coli$ RNA polymerase contains a small subunit termed omega ($\omega$). See FIG. 3A. This subunit consists of 91 amino acids with a molecular weight of 10,105. Its cloning has been previously reported (Gentry et al. (1986) $Gene$ 48:33–40). We fused the $\omega$ coding sequence in frame to the C-terminus of $\lambda$cI. See FIG. 3B. In bacterial strains lacking wildtype $\omega$, the $\lambda$cI-$\omega$ fusion protein was able to drive expression of a $\beta$-gal reporter gene having a $\lambda$cI operator (See FIG. 3C). FIG. 3C also illustrates that $\lambda$cI itself was unable efficiently induce expression of the reporter gene. Moreover, wildtype $\omega$ can effectively compete for binding to the holoenzyme complex, and can inhibit the ability of $\lambda$cI-$\omega$ to induce expression of the reporter gene.

Figure 3B:
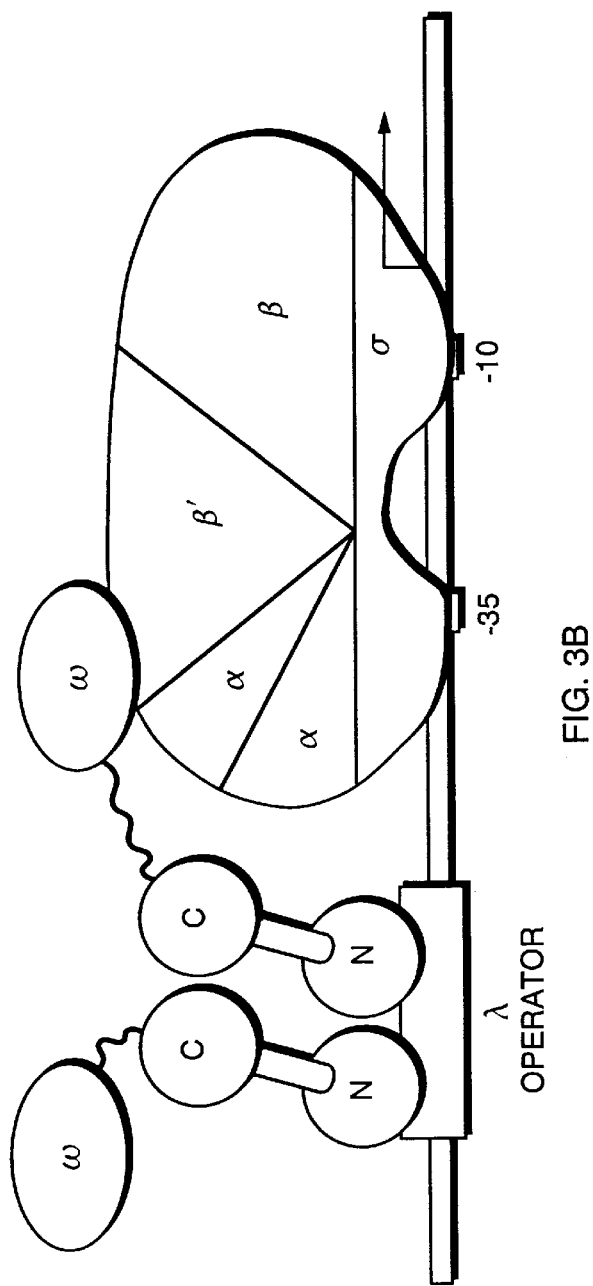
FIG. 3B illustrates the covalent linkage of the ω subunit to the λcI protein in the form of a λcI-ω fusion protein.
Figure 3C:
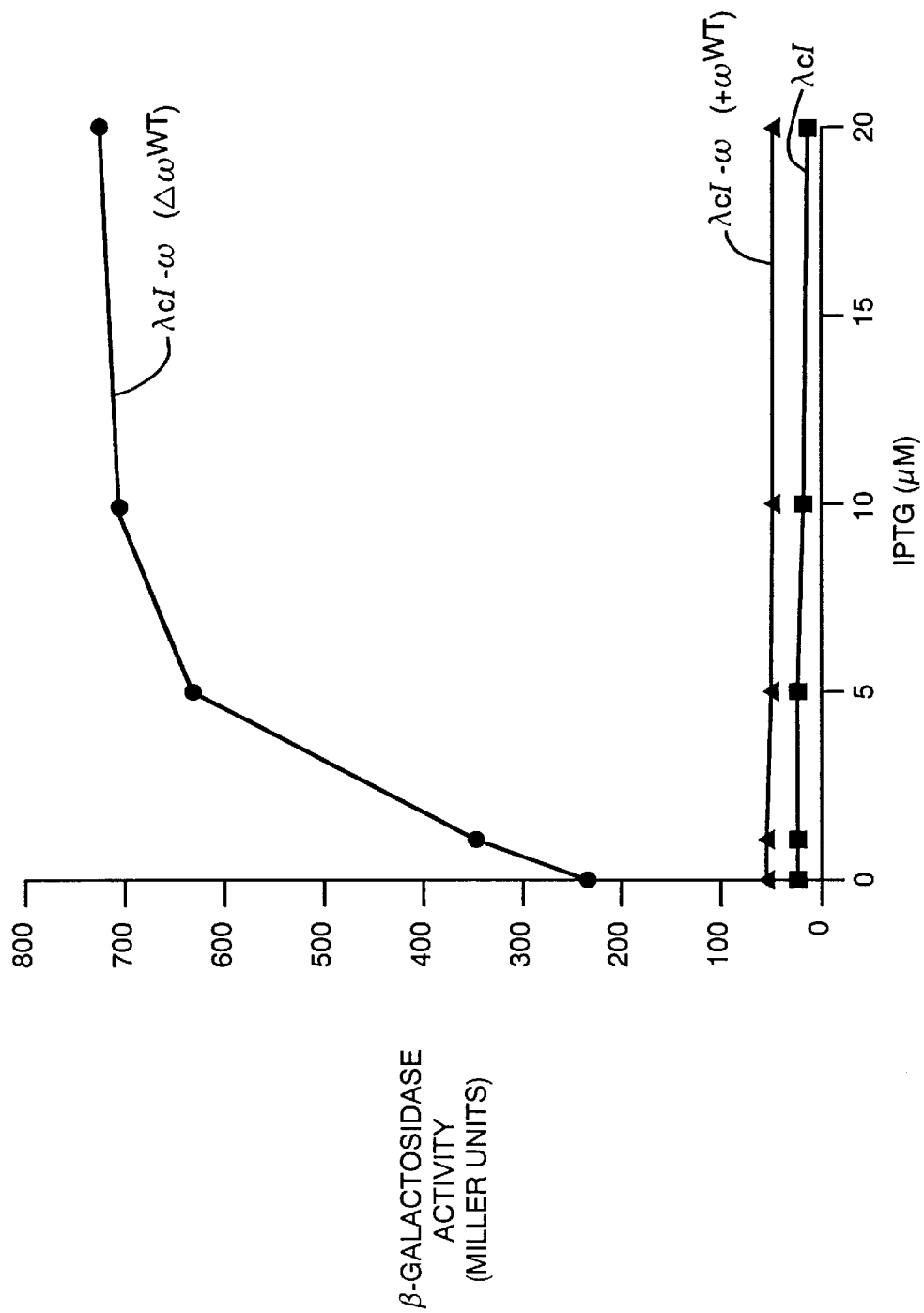
FIG. 3C is a graph indicating the ability of the λcI-ω fusion protein to drive expression of a reporter gene having a λ operator.

The single hybrid embodiment illustrated by FIGS. 3B–C suggests another aspect of the present invention. While two hybrid assays (or perhaps more accurately, multiple hybrid assays) have been described, the single hybrid approach has a wide range of uses. For example, it can be used to clone binding domains specific for a given nucleotide sequence, or alternatively to identify the nucleotide sequence specificity for a known DBD.

To further illustrate, a variegated library of nucleic acid sequences, e.g. including coding sequences for potential DNA binders, are cloned into a chimeric gene encoding a fusion protein that also has an activation domain (e.g., a PID). In the presence of a reporter gene having a defined DBD responsive element, those fusion proteins of the library that can bind the DBD responsive element can cause reporter gene expression. Likewise, a library of reporter genes can be generated in which a portion of the upstream regulatory sequence is varied. The ability of the DBD of the fusion protein to bind to any particular sequence can be detected by reporter read-out, and the consensus sequence specificity of the DBD determined by analysis of those reporter genes which were activated by the fusion protein.

In still other embodiments, the assay can be derived with a DBD and recognition element known to interact. Such embodiments are useful for screening for compounds which potentiate or inhibit the DNA binding activity of the DBD, e.g., which compounds may be useful for regulating gene expression in vivo.

Figure 3D:
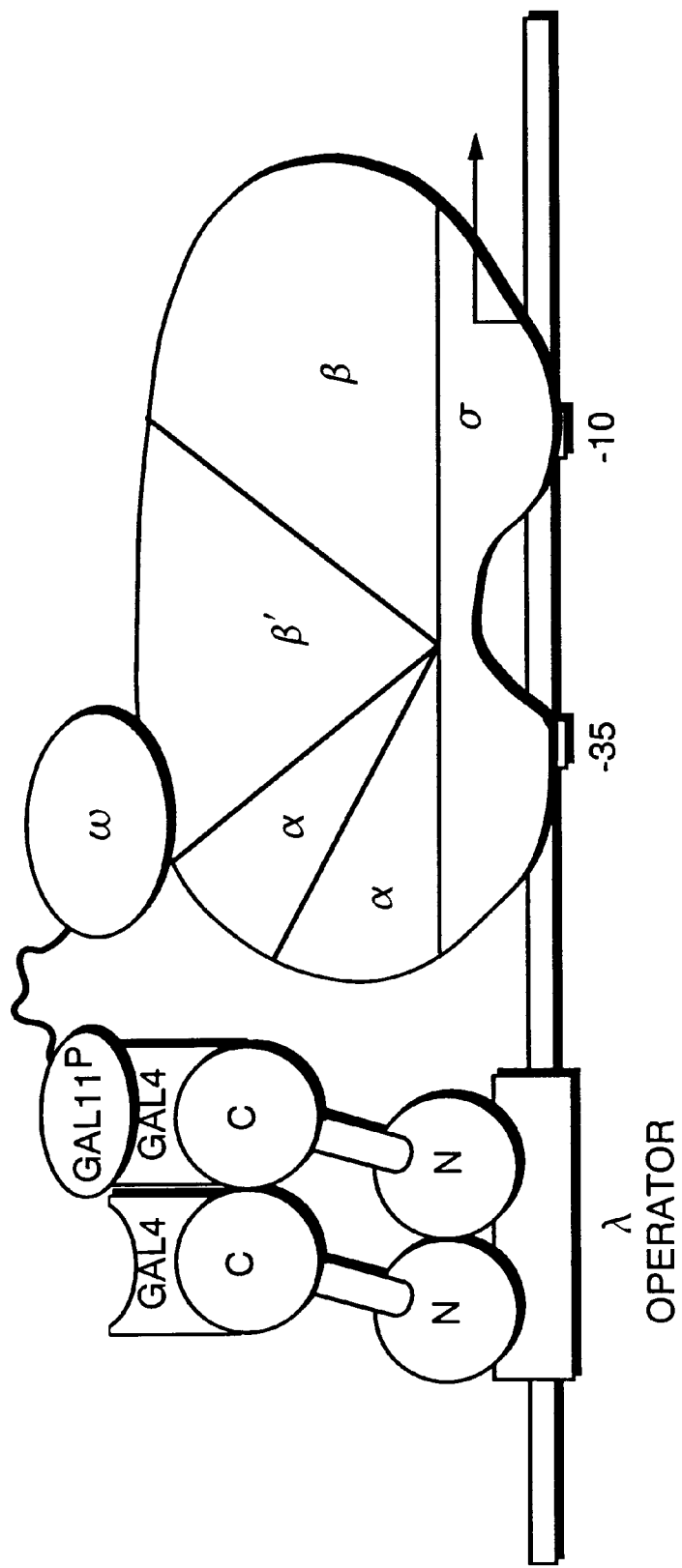
FIG. 3D depicts an ITS using the ω subunit in a $GAL11^P$-ω fusion protein.
Figure 3E:
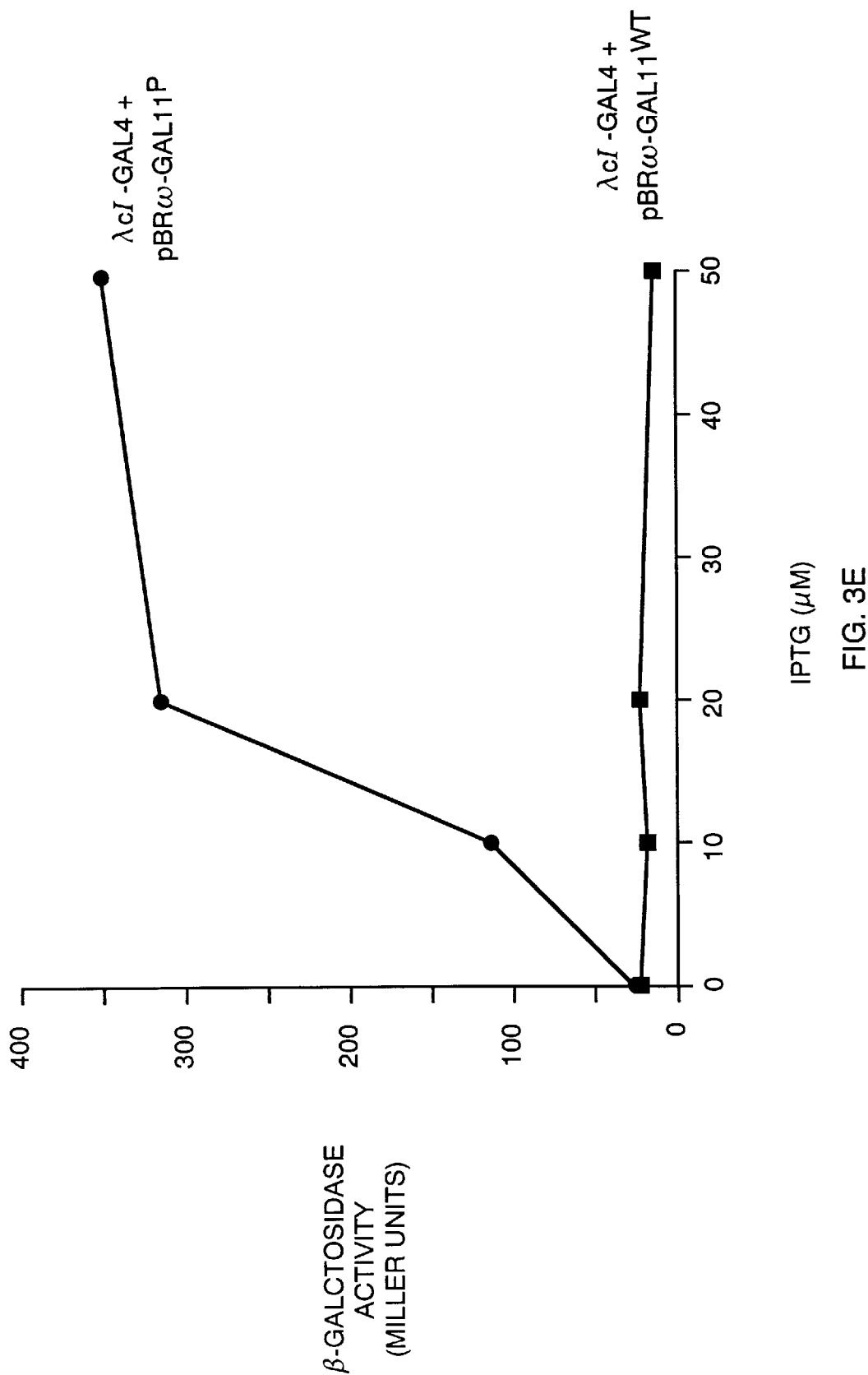
FIG. 3E is a graph showing that co-expression of the $GAL11^P$-ω fusion protein with a λcI-GAL4 fusion protein can activate the expression of a reporter gene under the transcriptional control of a λ operator.

To demonstrate the ability of the $\omega$ subunit to be utilized in the subject ITS (the two hybrid), the coding sequence for $\omega$ was fused to a portion of the coding sequence for GAL11$^P$ (see FIG. 3D). A fusion protein comprised of the $\lambda$cI protein having the dimerization region of GAL4 fused at its C-terminus was constructed. As demonstrated in FIG. 3E, the co-expression of both fusion proteins can activate the expression of a reporter gene under the transcriptional control of a $\lambda$cI operator. Substitution of the wildtype GAL11 sequence for the GAL11$^P$ sequence results in loss of transcriptional activity of the co-expressed fusion proteins.

Additionally, given the general conservation of the polymerase subunits amongst bacteria, the present invention also specifically contemplates prey fusion proteins derived with polymerase interaction domains of RNA polymerase subunits from other bacteria, e.g., $Staphylococcus$ $aureus$ (Deora et al. (1995) Biochem Biophys Res Commun 208:610), $Bacillus$ $subtilis$, etc.

In an alternative embodiment, instead of a polymerase interaction domain, the prey fusion protein can include an activation domain of a transcriptional activator protein. The bait fusion protein, by forming DNA bound complexes with the prey fusion protein, can indirectly recruit RNA polymerase complexes to the promoter sequences of the reporter gene, thus activating transcription of the reporter gene. To illustrate, the activation domain can be derived from such transcription factors as PhoB or OmpR. The critical consideration in the choice of the activation domain is its ability to interact with RNA polymerase subunits or complexes in the host cell in such a way as to be able to activate transcription of the reporter gene.

The prey fusion proteins can differ in the polymerase interaction domains or target surfaces they include, and in whether they contain other useful moieties such as epitope tags, oligomerization domain, etc. There are also a wide variety of prey polypeptides which can be selected to generate the fusion protein. The prey polypeptide can be derived from all or a portion of a known protein or a mutant thereof, all or a portion of an unknown protein (e.g., encoded by a gene cloned from a cDNA library), or a random polypeptide sequence (or be a random sequence included in a larger polypeptide sequence).

To isolate DNA sequences encoding novel interacting proteins, members of a DNA expression library (e.g., a cDNA or synthetic DNA library, either random or intentionally biased) can be fused in-frame to the activation tag (e.g., the polymerase interaction domain or activation domain) to generate a variegated library of prey fusion proteins. Those library-encoded proteins that physically interact with the promoter-bound bait fusion protein detectably alter expression of the reporter gene and provide a ready assay for identifying a particular DNA clone encoding an interacting protein of interest.

In an exemplary embodiment, cDNAs may be constructed from any mRNA population and inserted into an equivalent expression vector. Such a library of choice may be constructed de novo using commercially available kits (e.g., from Stratagene, La Jolla, Calif.) or using well established preparative procedures (see, for example, *Current Protocols in Molecular Biology*, Eds. Ausubel et al. John Wiley & Sons: 1992). Alternatively, a number of cDNA libraries (from a number of different organisms) are publicly and commercially available; sources of libraries include, e.g., Clontech (Palo Alto, Calif.) and Stratagene (La Jolla, Calif.). It is also noted that prey polypeptide need not be naturally occurring full-length proteins. In certain embodiments, prey proteins are encoded by synthetic DNA sequences, are the products of randomly generated open reading frames, are open reading frames synthesized with an intentional sequence bias, or are portions thereof. Preferably, such short randomly generated sequences encode peptides between, for example, 4 and 60 amino acids in length.

It will be appreciated by those skilled in the art that many variations of the prey and bait fusion proteins can be constructed and should be considered within the scope of the present invention. For example, it will be understood that, for screening polypeptide libraries, the library can be cloned into either the bait or prey fusion proteins. In this sense, the terms "prey" and "bait" are merely convenient names for fusion proteins with activation tags and DNA binding domains, respectively. Indeed, in certain embodiments it will be desirable to derive the prey fusion protein with a fixed test polypeptide rather than a variegated library on the grounds that the single prey fusion protein can be easily tested for its ability to be assembled into a functional RNA polymerase enzyme. Moreover, the bait fusion protein is likely to be less sensitive to variations caused by the different peptides of the library than is the prey fusion protein. In such embodiments, a variegated bait polypeptide library can be used to create a library of bait fusion proteins to be tested for interaction with a particular prey protein.

While it will generally be desirable for the DBD and bait polypeptide portions of the bait fusion protein, and activation tag and prey polypeptide portions of the prey fusion protein to be derived from different, e.g., heterologous, proteins, the present invention also contemplates embodiments of the instant assay wherein one of the two bait or prey proteins is a naturally occurring protein rather than a heterologous fusion protein. As an illustration, the bait protein can be a dimeric transcriptional activator which undergoes a higher order tetramerization reaction (for example, the λcI protein—See FIGS. 1A and 1B). That dimer-dimer interaction can be selected as the target of an assay to identify an agent which selectively disrupts the inter-dimer contacts. In such embodiments, the full-length transcriptional activator can serve the role of the bait protein, and the prey fusion protein can include, for example, that portion of the transcriptional activator which is involved in the formation of tetrameric complexes.

Moreover, either or both the prey and bait proteins, if desired, may include epitope tags (e.g., portions of the c-myc protein or the flag epitope available from Immunex). The epitope tag can facilitate a simple immunoassay for fusion protein expression, e.g. to detect the presence and folding of the fusion protein.

In other embodiments of the subject ITS, particularly those in which a polypeptide library is displayed on either the bait or prey protein, the fusion proteins can be generated to include, in addition to the test polypeptide sequences, another known polypeptide sequence. Thus, a prey fusion protein can be generated having the following exemplary formula: A-B-C, where A is the α-NTD, B is a control binding sequence (such as the C terminal domain [CTD] of λcI), and C is the test polypeptide sequence. To assure oneself that the fusion protein is correctly folded, the fusion protein can be first tested in an ITS using λcI CTD in the bait protein—the C terminal domain included in the prey protein providing a means for binding (via dimer-dimer interaction) with the bait. Prey fusion proteins which pass this control ITS can then be sampled in an ITS wherein bait is constructed with test polypeptide(s). Of course it will be appreciated that the order of the control and test polypeptides can be reversed.

In other embodiments, the construct encoding the prey (or bait) fusion protein can include a promoter for in vitro translation (e.g., a T7 promoter) of the target polypeptide. c.f., Yavuzer et al. (1995) *Gene* 165:93. Such constructs can be used to eliminate subcloning steps necessary to carry out certain validation assays often undertaken after the initial identification of the protein in the interaction trap, e.g., to determine if the binding of the two hybrid proteins is truly the result of an interaction between the bait and prey polypeptides per se.

In another aspect of the present invention, the DNA sequence encoding the prey protein (or alternatively the bait protein) is embedded in a DNA sequence encoding a conformation-constraining protein (i.e., a protein that decreases the flexibility of the amino and carboxy termini of the prey protein). Such embodiments are preferred where the prey polypeptide is a relatively short peptide, e.g., 5–25 amino acid residues. In general, conformation-constraining proteins act as scaffolds or platforms, which limit the number of possible three dimensional configurations the peptide or protein of interest is free to adopt. Preferred examples of conformation-constraining proteins are thioredoxin or other thioredoxin-like sequences, but many other proteins are also useful for this purpose. Preferably, conformation-constraining proteins are small in size (generally, less than or equal to 200 amino acids), rigid in structure, of known three dimensional configuration, and are able to accommodate insertions of proteins of interest without undue disruption of their structures. A key feature of such proteins is the availability, on their solvent exposed surfaces, of locations where peptide insertions can be made (e.g., the thioredoxin active-site loop).

As mentioned above, one preferred conformation-constraining protein according to the invention is thioredoxin or other thioredoxin-like proteins. The three dimensional structure of *E. coli* thioredoxin is known and contains several surface loops, including a distinctive Cys-Cys active-site loop between residues Cys33 and Cys36 which protrudes from the body of the protein. This Cys-Cys active-site loop is an identifiable, accessible surface loop region and is not involved in interactions with the rest of the protein which contribute to overall structural stability. It is therefore a good candidate as a site for prey protein insertions. Both the amino- and carboxyl-termini of *E. coli* thioredoxin are on the surface of the protein and are also readily accessible for fusion construction.

It may be preferred for a variety of reasons that prey (or bait) polypeptides be fused within the active-site loop of thioredoxin or thioredoxin-like molecules. The face of thioredoxin surrounding the active-site loop has evolved, in keeping with the protein's major function as a nonspecific protein disulfide oxido-reductase, to be able to interact with a wide variety of protein surfaces. The active-site loop region is found between segments of strong secondary structure and this provides a rigid platform to which one may tether prey proteins. A small prey protein inserted into the active-site loop of a thioredoxin-like protein is present in a region of the protein which is not involved in maintaining tertiary structure. Therefore the structure of such a fusion protein is stable. Thus, relatively short peptides may be displayed as part of the prey fusion protein by virtue of the fusion of the thioredoxin protein to a polymerase interaction domain. Such embodiments are useful for screening peptide libraries for interactors with a particular target bait protein.

The subject assay can also be used to generate antibody equivalents for specific determinants, e.g., such as single chain antibodies, minibodies or the like. Indeed, the subject method can be used to identify a novel binding partner for a given epitope/determinant where the new binding partner is a completely artificial polypeptide. For example, a target polypeptide (or epitope thereof) for which an antibody or antibody equivalent is sought can be displayed on either the bait or prey fusion protein. A library of potential binding partners can be arrayed on the other fusion protein, as appropriate. Interactions between the target polypeptide and members of the library of binding partners can be detected according to methods described herein. Thus, the present invention provides a convenient method for identifying recombinant nucleic acid sequences which encode proteins useful in the replacement of, e.g., monoclonal antibodies.

In another embodiment of the subject ITS, the system can be used to identify proteolytic activities which cleave a given polypeptide sequence, or to identify the sequence specificity for a given protease. For example, in the embodiment of the subject ITS illustrated in FIG. 1B, a desired cleavage sequence can be introduced into the bait or prey fusion proteins such that, upon cleavage of the fusion protein at that sequence, the DNA localization of the bait or prey protein is lost. To further illustrate, a substrate sequence for a proteolytic activity can be engineered into the linker sequence separating the N- and C-25 terminal domains of the bait protein shown in FIG. 1B. In the absence of proteolysis of that sequence, the intact prey and bait proteins induce expression of a reporter gene (or "inverter" gene as appropriate). The presence in the cell of a proteolytic activity which recognizes the substrate sequence can result in cleavage of the bait protein, separating the DBD from that portion of the protein which interacts with the prey fusion protein. Such embodiments of the ITS can be used to screen libraries of proteolytic proteins, e.g., derived from cDNA libraries, or generated by combinatorial mutagenesis of existing enzymes.

In other embodiments, peptide libraries can be engineered into one of the fusion proteins and proteolysis of the fusion protein by a predetermined proteolytic activity used to identify the sequence specificity of the proteolytic activity and/or optimize the sequence for a substrate or inhibitor for the proteolytic activity. For example, a variety of proteases have been identified as being involved in various disease states. In many instances, the substrate specificity for a protease has not yet been fully determined or optimized. Utilizing the subject ITS, the substrate specificity for a given protease can be accurately determined, and selective substrates or inhibitors, as appropriate, can be developed based on that sequence information. Alternatively, potential inhibitor libraries can be screened for compounds which block cleavage of the fusion protein.

In still other embodiments, the subject ITS can be derived to score for heteromeric combinations of three or more proteins by providing two or more different bait fusion proteins and/or two or more different prey fusion proteins in the same system, i.e., at least three different fusion proteins. This concept is illustrated by an example using α-NTD fusion proteins.

The α subunit of *E. coli* RNA polymerase plays a key role in assembly of the core enzyme. In previous studies, it has been demonstrated that the holoenzyme includes two α subunits, only one of which interacts with β. Assembly-deficient mutants of α have been identified, such as α-R45A (having substituted Ala for Arg at residue 45). This mutant dimerizes, but does not associate with the β subunits. When over-expressed in cells also expressing wildtype α, the equilibrium of the system favors formation of holoenzyme complexes which are heterologous with respect to α, e.g., including one wildtype and one R45A mutant subunit. Thus, making fusion proteins with a DNA binding domain, and with each of the wildtype and R45A α-NTDs, the system can accommodate three different polypeptide sequences which can be tested for simultaneous interactions. In other embodiments, fusing the same polypeptide sequence to the two different α-NTD sequences can be used to distinguish oligomerization mechanisms, e.g., distinguish tetramerization from pairwise dimerization.

In other embodiments, the multimeric system can be generated by creating multiple fusion proteins with polymerase subunits. As described above, each of the α and ω subunits can be engineered to be simultaneously expressed as fusion proteins.

V. Reporter gene constructs

The reporter gene of this invention ultimately measures the end stage of the above described cascade of events, e.g., transcriptional modulation, and, if desired, permits the isolation of ITS cells on the basis of that criterion. Accordingly, in practicing one embodiment of the assay, a reporter gene construct is inserted into the reagent cell in order to generate a detection signal dependent on interaction of the bait and prey fusion proteins. Typically, the reporter gene construct will include a reporter gene in operative linkage with one or more transcriptional regulatory elements which include, or are linked to, a DBD recognition element for the DBD of the bait fusion protein, with the level of expression of the reporter gene providing the prey protein interaction-dependent detection signal. Many reporter genes and transcriptional regulatory elements useful in the subject ITS are known to those of skill in the art and others may be readily identified or synthesized. Moreover, DBD recognition elements are known in the art for a wide variety of DNA binding domains which may used to construct the bait proteins of the present invention. Exemplary recognition elements include the λ operator, the LexA operator, the pho box, and the like.

A "reporter gene" includes any gene that expresses a detectable gene product, which may be RNA or protein. Preferred reporter genes are those that are readily detectable. The reporter gene may also be included in the construct in the form of a fusion gene with a gene that includes desired transcriptional regulatory sequences or exhibits other desirable properties.

Examples of reporter genes include, but are not limited to CAT (chloramphenicol acetyl transferase) (Alton and Vapnek (1979), Nature 282:864–869) luciferase, and other enzyme detection systems, such as beta-galactosidase; firefly luciferase (deWet et al. (1987), Mol. Cell. Biol. 7:725–737); bacterial luciferase (Engebrecht and Silverman (1984), PNAS 1:4154–4158; Baldwin et al. (1984), Biochemistry 23:3663–3667); phycobiliproteins (especially phycoerythrin); green fluorescent protein (GFP: see Valdivia et al. (1996) Mol Microbiol 22:367–78; Cormack et al. (1996) Gene 173 (1 Spec No): 33–8; and Fey et al. (1995) Gene 165:127–130; alkaline phosphatase (Toh et al. (1989) Eur. J Biochem. 182:231–238, Hall et al. (1983) J. Mol. Appl. Gen. 2:101), secreted alkaline phosphatase (Cullen and Malim (1992) Methods in Enzymol. 216:362–368). Other examples of suitable reporter genes include those which encode proteins conferring drug/antibiotic resistance to the host bacterial cell, or which encode proteins required to complement an auxotrophic phenotype. A preferred reporter gene is the spc gene, which confers resistance to spectinomycin.

The amount of transcription from the reporter gene may be measured using any method known to those of skill in the art to be suitable. For example, specific mRNA expression may be detected using Northern blots or specific protein product may be identified by a characteristic stain or an intrinsic activity.

In preferred embodiments, the gene product of the reporter is detected by an intrinsic activity associated with that product. For instance, the reporter gene may encode a gene product that, by enzymatic activity, gives rise to a detection signal based on color, fluorescence, or luminescence.

The amount of expression from the reporter gene is then compared to the amount of expression in either the same cell in the absence of a test compound or it may be compared with the amount of transcription in a substantially identical cell that lacks heterologous DNA, such as the gene encoding the prey fusion protein. Any statistically or otherwise significant difference in the amount of transcription indicates that the prey fusion protein interacts with the bait fusion protein.

In other preferred embodiments, the reporter gene provides a selection method such that cells in which the reporter gene is activated have a growth advantage. For example the reporter could enhance cell viability, e.g., by relieving a cell nutritional requirement, and/or provide resistance to a drug. For example the reporter gene could encode a gene product which confers the ability to grow in the presence of a selective agent, e.g., chorlamphenicol or kanamycin.

In bacteria, suitable positively selectable (beneficial) genes include genes involved in biosynthesis or drug resistance. Countless other genes are potential selective markers. Certain of the above are involved in well-characterized biosynthetic pathways. In the simplest case, the cell is auxotrophic for an amino acid, such as histidine (requires histidine for growth), in the absence of activation of the reporter gene. Activation leads to synthesis of an enzyme required for biosynthesis of the amino acid and the cell becomes prototrophic for that amino acid (does not require an exogenous source). Thus the selection is for growth in the absence of that amino acid in the culture media.

Another class of useful reporter genes encode cell surface proteins for which antibodies or ligands are available. Expression of the reporter gene allows cells to be detected or affinity purified by the presence of the surface protein.

In appropriate assays, so-called counterselectable or negatively selectable genes may be used.

The marker gene may also be a screenable gene. The screened characteristic may be a change in cell morphology, metabolism or other screenable features. Suitable markers include β-galactosidase, alkaline phosphatase, horseradish peroxidase, luciferase, bacterial green fluorescent protein,; secreted alkaline phosphatase (SEAP); and chloramphenicol transferase (CAT). Some of the above can be engineered so that they are secreted (although not β-galactosidase). A preferred screenable marker gene is β-galactosidase; bacterial cells expressing the enzyme convert the colorless substrate Xgal into a blue pigment.

In general, many of the embodiments of the ITS described above rely upon expression the reporter as a positive readout, typically manifested either (1) as an enzyme activity (e.g., β-galactosidase) or (2) as enhanced cell growth on a defined medium (e.g., antibiotic resistance). Thus, these methods are suited for identifying a positive interaction of the bait and prey polypeptides, but are not well suited for identifying agents or conditions which inhibit intermolecular association between two polypeptide sequences. In part, this is because a failure to obtain expression of the reporter gene can result from many events which do not stem from a specific inhibition of binding of the two hybrid proteins. For example, an ITS using a reporter gene that stimulates growth under defined conditions theoretically can be used to screen for agents that inhibit the intermolecular association of the two hybrid proteins, but it will be difficult or impossible to discriminate agents that specifically inhibit the association of the two hybrid proteins from agents which simply inhibit cell growth. Thus, an agent which is toxic to the bacterial cell will prevent cell growth without specifically inhibiting the interaction of two hybrid proteins and will score falsely as a positive hit. Similarly, an ITS using a lacZ reporter gene or the like, or a cytotoxic gene, will falsely score general transcription or translation inhibitors as being inhibitors of two hybrid protein binding. Thus, ITS embodiments that produce a positive readout contingent upon intermolecular binding of the bait and prey proteins are generally not suitable for screening for agents which inhibit binding of the two hybrid proteins.

To avoid such confounding results, the ITS format can be modified slightly to provide a "reverse ITS". In the reverse ITS, the reporter gene encodes a transcriptional repressor which is expressed upon interaction of the bait and prey proteins. However, the host cell also includes a second reporter gene which, but for an operator sequence responsive to the repressor protein produced by the first reporter gene, would otherwise be expressed. Thus, the gene product of the first reporter gene regulates expression of the second reporter gene, and the expression of the latter provides a means for indirectly scoring for the expression of the former. Essentially, the first reporter gene can be seen as a signal inverter.

In this exemplary system, the bait and prey proteins positively regulate expression of the first reporter gene. Accordingly, where the first reporter gene is a repressor of expression of the second reporter gene, relieving expression of the first reporter gene by inhibiting the formation of complexes between the bait and prey proteins concomitantly relieves inhibition of the second reporter gene. For example, the first reporter gene can include the coding sequences for λcI. The second reporter gene can accordingly be a positive signal, such as providing for growth (e.g., drug selection or auxotrophic relief), and is under the control of a promoter which is constitutively active, but can be repressed by λcI. In the absence of an agent which inhibits the interaction of the bait and prey protein, the λcI protein is expressed. In turn, that protein represses expression of the second reporter gene. However, an agent which disrupts binding of the bait and prey proteins results in a decrease in λcI expression, and consequently an increase in expression of the second reporter gene as λcI repression is relieved. Hence, the signal is inverted.

In yet another embodiment for detecting agents which disrupt the bait-prey interaction, it is envisioned that under certain conditions the interaction between bait and prey fusion proteins might result in transcription repression rather than activation. For example, it is speculated that sufficiently strong binding between a bait fusion protein and a prey fusion protein may impede the escape of the polymerase from the promoter, which escape is required for elongation of a transcript, thus repressing transcription. In particular, a strong interaction between the bait and prey proteins, combined with a strong promoter (e.g., one which is efficient at binding the polymerase complex even in the absence of transcription factors) may result in repression of reporter gene expression. Under these conditions an inhibitor of bait-prey complex formation will, over a certain concentration range, cause the effective association constant of the complex to be reduced sufficiently to result in relief of the repression and concomitant transcription of the reporter gene. At higher concentrations, inhibitors of the bait-prey complex may result in inhibition (or return to basal levels) of transcription by the loss of bait-prey complexes. Thus, in one embodiment, the candidate agent can be spotted on a lawn of reagent cells plated on a solid media. The diffusion of the candidate agent through the solid medium surrounding the site at which it was spotted will create a diffusional effect. For agents which inhibit the formation of bait-prey complexes, a halo of reporter gene expression would be expected in an area which corresponds to concentrations of the agent which offset the effect of the repression due to strong association between the two hybrid proteins, but which are not so great as to substantially inhibit the formation of bait-prey complexes.

Still another consideration in generating the reporter gene construct concerns the placement of the DBD recognition element relative to the reporter gene and other transcriptional elements with which it is associated. In most embodiments, it will be desirable to position the recognition element at an inert position. In some instances, the axial position of the DBD relative to the promoter sequences can be important.

In certain embodiments, the sensitivity of the ITS can be enhanced for detecting weak protein-protein interactions by placing the DBD recognition sequence at a position permitting secondary interactions (if any) between other portions of the bait fusion protein and the RNA polymerase complex. For example, as described in the appended examples, an apparent synergistic effect was observed when the λ operator was moved closer to the promoter (i.e. at its normal position). While not wishing to be bound by any particular theory, this synergism is speculated to be the result of a bait-prey interaction and second interaction between DBD of λcI and a second polymerase subunit (σ).

It will also be understood by those skilled in the art that the sensitivity to the strength of the interactions between the bait and prey proteins can be "tuned" by adjusting the sequence of the recognition element. For example, the use of a strong λ operator instead of weak can improve the sensitivity of the assay to weak bait-prey interactions, as well as help to overcome lack of dimerization if no dimerization signals are included in the bait fusion protein.

In particular embodiments, it may desirable to provide two or more reporter gene constructs which are regulated by interaction of the bait and prey proteins. The simultaneous expression of the various reporter genes provides a means for distinguishing actual interaction of the bait and prey proteins from, e.g., mutations or other spurious activation of the reporter gene.

VI. Host cells

Exemplary prokaryotic host cells are gram-negative bacteria such as *Escherichia coli,* or gram-positive bacteria such as *Bacillus subtilis.*

Recognized prokaryotic hosts include bacterial strains of Escherichia, Bacillus, Streptomyces, Pseudomonas, Salmonella, Serratia, Shigella and the like. The prokaryotic host must be compatible with the replicon and control sequences in the expression plasmid.

Preferred prokaryotic host cells for use in carrying out the present invention are strains of the bacteria Escherichia, although Bacillus and other genera are also useful. Techniques for transforming these hosts and expressing foreign genes cloned in them are well known in the art (see e.g., Maniatis et al. and Sambrook et al., ibid.). Vectors used for expressing foreign genes in bacterial hosts will generally contain a selectable marker, such as a gene for antibiotic resistance, and a promoter which functions in the host cell. Appropriate promoters include trp (Nicholset al. (1983) *Meth. Enzymol.* 101:155–164), lac (Casadaban et al. (1980) *J. Bacteriol.* 143:971–980), and phage gamma promoter systems (Queen (1983) *J. Mol. Appl. Genet.* 2:1–10). Plasmids useful for transforming bacteria include pBR322 (Bolivar et al. (1977) *Gene* 2:95–113), the pUC plasmids (Messing (1983) *Meth. Enzymol.* 101:20–77), Vieira and Messing (1982) *Gene* 19:259–268), pCQV2 (Queen, supra), pACYC plasmids (Chang et al. (1978) *J. Bacteriol* 134:1141), pRW plasmids (Lodge et al. (1992) *FEMS Microbiol Lett* 95:271), and derivatives thereof.

The choice of appropriate host cell will also be influenced by the choice of detection signal. For instance, reporter constructs, as described below, can provide a selectable or screenable trait upon transcriptional activation (or inactivation). The reporter gene may be an unmodified gene already in the host cell pathway, such as sporulation genes. It may be a host cell gene that has been operably linked to a "bait-responsive" promoter. Alternatively, it may be a heterologous gene that has been so linked. Suitable genes and promoters are discussed above. Accordingly, it will be understood that to achieve selection or screening, the host cell must have an appropriate phenotype. For example, introducing a histidine biosynthesis gene into a bacterial cell that has a wild-type form of that gene would frustrate genetic selection. Thus, to achieve nutritional selection, an auxotrophic strain will be desired which is complemented by expression of the reporter gene.

In other embodiments, the host cell can be a eukaryotic cell, particularly a yeast cell, which has been engineered to express a sufficient number of the bacterial polymerase subunits necessary to induce (reporter) gene expression in the cell in a manner dependent on the bait and prey proteins and the bacterial RNA polymerase subunits. It may be desirable in such embodiments to include a nuclear localization signal as part of one or more of the bacterial proteins. Regulatory sequences for the recombinant expression of these proteins in eukaryotic cells may also need to be optimized.

VII. Exemplary Uses of the Prokaryotic ITS

The prokaryotic ITS of the present invention can be used, inter alia, for identifying protein-protein interactions, e.g., for generating protein linkage maps, for identifying therapeutic targets, and/or for general cloning strategies. As described above, the ITS can be derived with a cDNA library to produce a variegated array of bait or prey proteins which can be screened for interaction with, for example, a known protein expressed as the corresponding fusion protein in the ITS. In other embodiments, both the bait and prey proteins can be derived to each provide variegated libraries of polypeptide sequences. One or both libraries can be generated by random or semi-random mutagenesis. For example, random libraries of polypeptide sequences can be "crossed" with one another by simultaneous expression in the subject assay. Such embodiments can be used to identify novel interacting pairs of polypeptides.

Alternatively, the subject ITS can be used to map residues of a protein involved in a known protein-protein interaction. Thus, for example, various forms of mutagenesis can be utilized to generate a combinatorial library of either bait or prey polypeptides, and the ability of the corresponding fusion protein to function in the ITS can be assayed. Mutations which result in diminished (or potentiated) binding between the bait and prey fusion proteins can be detected by the level of reporter gene activity. For example, mutants of a particular protein which alter interaction of that protein with another protein can be generated and isolated from a library created, for example, by alanine scanning mutagenesis and the like (Ruf et al., (1994) *Biochemistry* 33:1565–1572; Wang et al., (1994) *J. Biol. Chem.* 269:3095–3099; Balint et al., (1993) *Gene* 137:109–118; Grodberg et al., (1993) *Eur. J. Biochem.* 218:597–601; Nagashima et al., (1993) *J. Biol. Chem.* 268:2888–2892; Lowman et al., (1991) *Biochemistry* 30:10832–10838; and Cunningham et al., (1989) *Science* 244:1081–1085), by linker scanning mutagenesis (Gustin et al., (1993) *Virology* 193:653–660; Brown et al., (1992) *Mol. Cell Biol.* 12:2644–2652; McKnight et al., (1982) *Science* 232:316); by saturation mutagenesis (Meyers et al., (1986) *Science* 232:613); by PCR mutagenesis (Leung et al., (1989) *Method Cell Mol Biol* 1:11–19); or by random mutagenesis (Miller et al., (1992) *A Short Course in Bacterial Genetics,* CSHL Press, Cold Spring Harbor, N.Y.; and Greener et al., (1994) *Strategies in Mol Biol* 7:32–34). Linker scanning mutagenesis, particularly in a combinatorial setting, is an attractive method for identifying truncated (bioactive) forms of a protein, e.g., to establish binding domains.

In other embodiments, the ITS can be designed for the isolation of genes encoding proteins which physically interact with a protein/drug complex. The method relies on detecting the reconstitution of a transcriptional activator in the presence of the drug, such as rapamycin, FK506 or cyclosporin. If the bait and prey fusion proteins are able to interact in a drug-dependent manner, the interaction may be detected by reporter gene expression.

Another aspect of the present invention relates to the use of the prokaryotic ITS in the development of assays which can be used to screen for drugs which are either agonists or antagonists of a protein-protein interaction of therapeutic consequence. In a general sense, the assay evaluates the ability of a compound to modulate binding between the bait and prey polypeptides. Exemplary compounds which can be screened include peptides, nucleic acids, carbohydrates, small organic molecules, and natural product extract libraries, such as isolated from animals, plants, fungus and/or microbes.

In many drug screening programs which test libraries of compounds and natural extracts, high throughput assays are desirable in order to maximize the number of compounds surveyed in a given period of time. The subject ITS-derived screening assays can be carried out in such a format, and accordingly may be used as a "primary" screen. Accordingly, in an exemplary screening assay of the present invention, an ITS is generated to include specific bait and prey fusion proteins known to interact, and compound(s) of interest. Detection and quantification of reporter gene expression provides a means for determining a compound's efficacy at inhibiting (or potentiating) interaction between the bait and prey polypeptides. In certain embodiments, the approximate efficacy of the compound can be assessed by generating dose response curves from reporter gene expression data obtained using various concentrations of the test compound. Moreover, a control assay can also be performed to provide a baseline for comparison. In the control assay, expression of the reporter gene is quantitated in the absence of the test compound.

In an illustrative embodiment, the ITS assay can be used to identify cyclosporin or rapamycin mimetics by screening for agents which potentiate the interaction of an FK506 binding protein (FKBP) and a cyclophilin or TOR1 protein. For example, rapamycin-like drugs can be identified by the present invention which have enhanced tissue-type or cell-type specificity relative to rapamycin. The identification of such compounds can be enhanced by the use of differential screening techniques which detect and compare drug-mediated formation of two or more different types of FKBP/cyclophilin or FKBP/TOR complexes. To further illustrate, by side-by-side comparison of assays generated with mammalian and yeast proteins, the subject ITS can be used to identify rapamycin mimetics which preferentially inhibit proliferation of yeast cells or other lower eukaryotes, but which have a substantially reduced effect on mammalian cells, thereby improving therapeutic index of the drug as an anti-mycotic agent relative to rapamycin.

In another exemplary embodiment, a therapeutic target devised as the bait-prey complex is expressed in the same cell with a peptide library with the goal of identifying peptides which potentiate or inhibit the bait-prey interaction. Many techniques are known in the art for expressing peptide libraries intracellularly. In one embodiment, the peptide library is provided as part of a chimeric thioredoxin protein, e.g., expressed as part of the active loop (supra).

In yet another embodiment, the bacterial ITS can be generated in the form of a diagnostic assay to detect the interaction of two proteins, e.g., where the gene from one is isolated from a biopsied cell. For instance, there are many instances where it is desirable to detect mutants which, while expressed at appreciable levels in the cell, are defective at binding other cellular proteins. Such mutants may arise, for example, from fine mutations, e.g., point mutants, which may be impractical to detect by the diagnostic DNA sequencing techniques or by the immunoassays. The present invention accordingly further contemplates diagnostic screening assays which generally comprise cloning one or more cDNAs from a sample of cells, and expressing the cloned gene(s) as part of an ITS under conditions which permit detection of an interaction between that recombinant gene product and a target protein. Accordingly, the present invention provides a convenient method for diagnostically detecting mutations to genes encoding proteins which are unable to physically interact with a "target" protein, which method relies on detecting the expression of the reporter gene in a bait/prey-dependent fashion as described above.

To illustrate, the subject ITS can be used to detect inactivating mutations of the CDK4/p16$^{INK42}$ a interaction. Recent discoveries have brought several cell-cycle regulators into sharp focus as factors in human cancer. Among the most conspicuous types of molecules to emerge from ongoing studies in this field are the cyclin-dependent kinase inhibitors such as p16. (Serrano et al. (1993) *Nature* 366:704; and Okamoto et al. (1994) *PNAS* 91:11045) The p16 protein has several hallmarks of a tumor suppressor and is perfectly positioned to regulate critical decisions in cell growth. The p16 gene appears to be a particularly significant target for mutation in sporadic tumors and in at least one form of hereditary cancer. In an exemplary embodiment of the diagnostic ITS, a first hybrid gene comprises the coding sequence for a DNA-binding domain fused in frame to the coding sequence for a "target" protein, e.g., CDK4 or CDK6. The second hybrid protein encodes a polymerase interaction domain fused in frame to a gene encoding the "sample" protein, e.g. a p16 gene (cDNA) amplified from a cell sample of a patient. If the target and sample proteins are able to interact, e.g., form a CDK/p16 complex, then RNA polymerase is recruited to the promoter of a reporter gene which is operably linked to a DBD recognition element, thereby causing expression of the reporter gene. The expression of the reporter gene can be compared against that observed when the sample protein is encoded by normal p16 coding sequences, e.g., which may be amplified from normal cells, e.g. isolated by similar protocols to the test sample.

Moreover, it will be apparent that the subject two hybrid assay can be used generally to detect mutations in other cellular proteins which disrupt protein-protein interactions. For example, it has been shown that the transcription factor E2F-4 is bound to the p130 pocket protein, and that such binding effectively suppresses E2F-4-mediated transactivation required for control of $G_0/G_1$ transition. Mutations in genes encoding either E2F-4 or p130 which result in disruption of this interaction can be detected in the subject assay.

Similarly, Rb and Rb-like proteins (such as p107) act to control cell-cycle progression through the formation of complexes with several cellular proteins. In fact, a recent article concerning familial retinoblastoma has reported a new class of Rb mutants found in retinal lesions, which mutants were defective in protein binding ("pocket") activity (see, for example, Kratzke et al. (1994) *Oncogene* 9:1321–1326). Moreover, mutant forms of c-myc have been demonstrated in various lymphomas, e.g., Burkitt lymphomas, which mutants are resistant to p107-mediated suppression. Accordingly, the diagnostic two hybrid assay of the present invention can be used to detect mutations in Rb or Rb-like proteins which disrupt binding to other cellular proteins, e.g., myc, E2F, c-Ab1, or upstream binding factor (UBF), or vice-versa.

In another embodiment, the subject diagnostic assay can be employed to detect mutations which disrupt binding of the p53 protein with other cellular proteins, as for example, the Wilm's tumor suppresser protein WT1. Recent observations by Maheswaran et al. (1993, *PNAS* 90:5100–5104) have demonstrated that p53 can physically interact with WT1, and that this interaction modulates the ability of each protein to transactivate their respective targets. In fact, in contrast to the proposed function of WT1 as a transcriptional repressor, potent transcriptional activation by WT1 of reporter genes driven by EGR1 in cells lacking wild type p53 indicates that transcriptional repression is not an intrinsic property of WT1. Instead, transcriptional repression by WT1 may result from its interaction with p53. Accordingly, mutations in p53 which do not affect the cellular concentration of this protein, but which rather down regulate its ability to bind to and repress WT1, may give rise to Wilm's tumors, and other disease states associated with deregulation of WT1.

In still another embodiment, the diagnostic two hybrid assay can be used to detect mutations in pairs of signal transduction proteins. For example, the present assay can be used to detect mutations in the ras protein that affect its ability to interact with other cellular proteins or mutations in other cellular proteins which affect their ability to interact with ras, e.g., ras GTPase activating proteins (GAPs).

The method of the present invention, as described above, may be practiced using a kit for detecting interaction between a target protein and a sample protein as described above. In an illustrative embodiment, the kit includes two vectors, a host cell, and (optionally) a set of primers for cloning one or more genes encoding sample proteins from a patient sample. The first vector may contain a promoter, a transcription termination signal, and other transcription and translation signals functionally associated with the first chimeric gene in order to direct the expression of the first chimeric gene. The first chimeric gene includes a DNA sequence that encodes a DNA-binding domain and a unique restriction site(s) for inserting a DNA sequence encoding either the target or sample protein, or a fragment thereof, in such a manner that the cloned sequence is expressed as part of a hybrid protein with the DNA-binding domain. The first vector also includes a means for replicating itself (e.g., an origin of replication) in the host cell. In preferred embodiments, the first vector also includes a first marker gene, the expression of which in the host cell permits selection of cells containing the first marker gene from cells that do not contain the first marker gene. Preferably, the first vector is a plasmid, though it may optionally be genomically integrated where the chimeric gene encodes the target protein.

The kit also includes a second vector which contains a second chimeric gene. The second chimeric gene also includes a promoter and other relevant transcription and translation sequences to direct expression of a second chimeric protein. The second chimeric gene includes a DNA sequence that encodes an activation tag and a unique restriction site(s) to insert a DNA sequence encoding either the target or sample protein (whichever is not cloned into the first chimeric gene), in such a manner that the cloned protein is capable of being expressed as part of a fusion protein with the activation tag. Again, as appropriate, the second vector can be genomically integrated.

In general, the kit will also be provided with one of the two vectors already including the target protein. For example, the kit can be configured for detecting mutations to a p16-gene which result in loss of binding to CDK4. Accordingly, the first vector could be provided with a CDK4 open reading frame fused in frame to the DNA-binding domain to provide a CDK4 bait protein. p16-gene open reading frames can be cloned from a cell sample and ligated into the second vector in frame with the polymerase interaction domain.

Where the kit also provides primers for cloning a p16-gene into the two hybrid assay vectors, the primers will preferably include restriction endonuclease sites for facilitating ligation of the amplified gene into the insertion site flanking the DNA-binding domain or activation tag.

Accordingly in using the kit, the interaction of the target protein and the sample protein in the host cell causes a measurably greater expression of the reporter gene than when the DNA-binding domain and the activation tag are present in the absence of an interaction between the two fusion proteins. The cells containing the two hybrid proteins are incubated in/on an appropriate medium and the cells are monitored for the measurable activity of the gene product of the reporter construct. A positive test for this activity is an indication that the target protein and the sample protein have interacted. Such interaction brings their respective DNA-binding domain and activation tag into sufficiently close proximity to cause efficient transcription of the reporter gene.

Exemplification

The invention, now being generally described, will be more readily understood by reference to the following examples, which are included merely for purposes of illustration of certain aspects and embodiments of the present invention and are not intended to limit the invention. See also Dove et al. (1997) Nature 386:627 which is specifically incorporated herein by reference.

The C-terminal domain of the alpha subunit of RNA polymerase ($\alpha$-CTD) mediates the effects of many transcriptional activators in bacteria, likely through direct contact. The $\alpha$-CTD was replaced with the C-terminal domain of the bacteriophage $\lambda$ repressor, a domain that forms dimers and higher order oligomers. It is then demonstrated that an artificial promoter bearing a single $\lambda$ operator in its upstream region is activated by $\lambda$ repressor in cells that express the hybrid $\alpha$ gene. The following examples further show that mutations in $\lambda$ repressor that weaken the CTD oligomerization interaction also decrease activation in the strain bearing the hybrid $\alpha$ gene. These findings show that the strength of an arbitrary protein-protein interaction determines the magnitude of gene activation. Thus, for at least certain promoters, recruitment of RNA polymerase to the DNA is sufficient for gene activation.

RNA polymerase in E. coli consists of an enzymatic core composed of subunits $\alpha$, $\beta$, and $\beta'$ in the stoichiometry $\alpha_2\beta\beta'$, and one of several alternative $\sigma$ factors responsible for specific promoter recognition. The $\alpha$ subunit, which initiates the assembly of RNA polymerase by forming a dimer, has two independently folded domains. The larger amino-terminal domain ($\alpha$-NTD) mediates dimerization and the subsequent assembly of polymerase. The carboxy-terminal domain ($\alpha$-CTD), which is tethered to the $\alpha$-NTD by a flexible linker region, interacts with a DNA sequence known as the "UP-element" that is found upstream of the −35 region of certain particularly strong promoters. The $\alpha$-CTD is also the target of action of a large class of transcriptional activators.

The Cyclic AMP Receptor Protein (CRP) is the most intensively studied example of a transcriptional activator that exerts its effect on the $\alpha$-CTD. Several lines of evidence indicate that CRP uses a well-defined activating region consisting of a nine amino acid surface-exposed loop to contact the $\alpha$-CTD directly when bound to its recognition site (centered at postion −61.5) upstream of the familiar lac promoter. In the case of CRP as well as several other activators, specific amino acid residues in the $\alpha$-CTD have been identified that are required for activation. The available evidence suggests that activation by this class of activators involves direct contact with one or another target region on the $\alpha$-CTD. However, this evidence does not establish whether the $\alpha$-CTD plays some special role or whether any protein-protein contact would suffice.

To address this question, the natural interaction between activator and $\alpha$-CTD was replaced with a different interaction involving a protein domain that does not ordinarily mediate transcriptional activation. To do this, the well-defined properties of the C-terminal domain (CTD) of the bacteriophage $\lambda$ repressor were relied upon.

The $\lambda$ repressor ($\lambda$cI) is a two-domain protein that functions as both a repressor and an activator of transcription. $\lambda$cI binds DNA as a dimer, and pairs of dimers bind cooperatively to adjacent operator sites (FIG. 1A). The N-terminal domain contacts the DNA and interacts with RNA polymerase when $\lambda$cI is bound at promoter $P_{RM}$, whereas the CTD mediates both dimer formation and the dimer-dimer interaction that results in cooperativity. A large number of $\lambda$cI mutants specifically defective for cooperative binding to DNA have been isolated and these mutants bear single amino acid substitutions in the CTD.

It was reasoned that if the $\alpha$-CTD was replaced with the $\lambda$cI-CTD, the resulting $\alpha$-cI fusion protein would display a dimeric target that could be contacted by an appropriately positioned $\lambda$cI dimer (FIG. 1B). This would test whether the same protein-protein interaction that ordinarily mediates the cooperative binding of pairs of $\lambda$cI dimers to the DNA would mediate transcriptional activation when the $\lambda$cI-CTD is tethered to the $\alpha$-NTD.

The hybrid $\alpha$ gene was created by replacing the gene segment encoding the $\alpha$-CTD with a gene segment encoding the $\lambda$cI-CTD. A derivative of the lac promoter bearing a single $\lambda$ operator ($O_R2$) in place of the CRP-binding site was created (centered 62 bps upstream of the transcription startpoint) (FIG. 1B). Ordinarily, $\lambda$cI activates transcription when bound at a unique position centered at position −42; as expected, therefore, $\lambda$cI does not activate transcription from this lac promoter derivative.

The lac promoter derivative was introduced in single copy into the chromosome of E. coli strain MC1000 F'lacI$^q$. Compatible vectors driving the expression of the hybrid $\alpha$ gene and the cI gene were also introduced into this strain. $\lambda$cI stimulated transcription from the lac promoter derivative a maximum of approximately 10-fold as measured by $\beta$-galactosidase assays. This stimulation was observed only in the presence of the hybrid $\alpha$ gene; in its absence $\lambda$cI repressed transcription slightly. Furthermore, expression of the $\alpha$-cI fusion protein had no significant effect on transcription from the lac promoter derivative in the absence of $\lambda$cI. Primer extension analysis confirmed that the stimulatory effect of $\lambda$cI reflected an increase in correctly initiated transcripts.

Our hypothesis concerning the mechanism of this activation predicts that a λcI mutant unable to bind cooperatively to the DNA would be unable to activate transcription in this artificial system. To test this prediction an experiment was designed using the λcI cooperativity mutant (λcI-D197G) that is unable to bind cooperatively to both adjacent and separated operator sites, but is otherwise fully functional (i.e. its binding to a single operator site in vivo is indistinguishable from that of wild type λcI). Unlike wild type λcI, this mutant failed to activate transcription from the lac promoter derivative in the presence of the hybrid α gene.

Furthermore, several λcI mutants with specific but less severe cooperativity defects were also utilized in similar experiments. Substitutions N148D and R196M weaken, but do not abolish, the dimer-dimer interaction responsible for cooperativity. Mutant R196M is more defective for cooperative binding than mutant N148D, and, like mutant D197G, both λcI-N148D and λcI-R196M behave indistinguishably from wild type λcI in binding to a single operator site in vivo. The two mutants stimulated transcription from the lac promoter derivative more weakly than wild type λcI, and the stronger cooperativity mutant also manifested a stronger activation defect.

The equilibrium dissociation constant for the interaction of λcI dimers in solution is about $10^{-6}$ M, and cooperative binding to DNA likely involves this same interaction. These results suggest that any protein-protein interaction of comparable strength involving a DNA-bound protein and a protein domain tethered to the α-NTD would bring about transcriptional activation. The analysis of the λcI cooperativity mutants indicates that the magnitude of the activation decreases as the dimer-dimer interaction is weakened. It is not known what would be the effect of increasing the strength of the dimer-dimer interaction. It will be interesting to learn how strong an interaction would result in maximal activation. It is possible that a sufficiently strong interaction might impede promoter clearance and, therefore, result in transcriptional repression rather than activation.

Our results indicate that a protein domain with no determinants for DNA-binding can mediate transcriptional activation when tethered to the α-NTD simply by providing a surface that can be contacted by a DNA-bound protein. The discovery of the DNA-binding capability of the α-CTD suggested that activators that interact with the α-CTD might help stabilize its association with DNA at promoters that lack an UP element. In support of this idea, footprinting studies have indicated that the interaction between CRP and the α-CTD at the lac promoter promotes the association of the α-CTD with the DNA adjacent to the CRP-binding site and upstream of the promoter −35 region. This observation has prompted the proposal that other, and perhaps all, activators that interact with the α-CTD function by recruiting the α-CTD to the DNA. These findings, however, imply that activation can occur in the absence of this recruitment.

This new protein-protein contact alone suffices for gene activation, suggesting that a DNA-bound activator can recruit the holoenzyme to a promoter simply by touching an available target surface. These findings in E. coli imply that in prokaryotes, activation can be elicited by a simple protein-protein contact involving a DNA-bound activator on the one hand and an available target surface within the RNA polymerase holoenzyme on the other.

λcI normally activates transcription at the λ$P_{RM}$ promoter using an activation patch on its N-terminal domain to contact the σ subunit of RNA polymerase. This contact requires that λcI be bound just upstream of the $P_{RM}$−35 region at a site centered at position −42. An experiment was designed to ask whether λcI bound at this position could use both its normal activation patch and its C-terminal domain to make simultaneous contacts with RNA polymerase in a strain expressing the α-cI fusion protein. This was found to work spectacularly well. Whereas λcI normally stimulates PRM transcription by a factor of less than 10, an approximately 100-fold stimulation in a strain expressing the α-cI fusion was observed.

This finding suggests that one could use this set up to detect extremely weak protein-protein interactions. In fact, the data with the D197G mutant shows that with this assay a weak residual interaction can be detected.

All of the above-cited references and publications are hereby incorporated by reference.

Equivalents

Those skilled in the art will recognize, or be able to ascertain using no more than routine experimentation, numerous equivalents to the specific polypeptides, nucleic acids, methods, assays and reagents described herein. Such equivalents are considered to be within the scope of this invention and are covered by the following claims.

We claim:

1. A method for detecting interaction between a first test polypeptide and a second test polypeptide, comprising
    i. providing an interaction trap system including a prokaryotic host cell which contains
        (a) a reporter gene operably linked to a transcriptional regulatory sequence which includes a binding site (DBD recognition element) for a DNA-binding domain,
        (b) a first chimeric gene which encodes a first fusion protein, the first fusion protein including a DNA-binding domain and first test polypeptide,
        (c) a second chimeric gene which encodes a second fusion protein, the second fusion protein including an activation tag and second test polypeptide,
    wherein interaction of the first fusion protein and second fusion protein in the host cell results in a measurable change in expression of the reporter gene; and
    ii. measuring expression of the reporter gene.

2. The method of claim 1 which futher comprises comparing the level of expression of the reporter gene to a level of expression in a control interaction trap system in which either one or both of the test polypeptides are absent or altered so as preclude interaction of the first and second fusion proteins.

3. The method of claim 1, wherein the activation tag is a polymerase interaction domain (PID) which forms active RNA polymerase complexes in the host cell.

4. The method of claim 1, wherein the host cell is selected from the group consisting of bacterial strains of Escherichia, Bacillzis, Streptomyces, Pseudomonas, Salmonella, Serratia and Shigella.

5. The method of claim 1, wherein the reporter gene encodes a gene product that gives rise to a detectable signal selected from the group consisting of: color, fluorescence, luminescence, a cell surface tag, cell viability, relief of a cell nutritional requirement, cell growth, and drug resistance.

6. The method of claim 1, wherein the reporter gene encodes a gene product selected from the group consisting of the spectinomycin (spc) gene product, chloramphenicol acetyl transferase, luciferase, β-galactosidase and alkaline phosphatase.

7. The method of claim 1, wherein at least one of the first and second test polypeptides are encoded by nucleic acids from a nucleic acid library.

8. The method of claim 1, wherein the DNA-binding domain is a naturally occurring DNA binding protein.

9. The method of claim 1, wherein the DNA-binding domain is an artificial polypeptide.

10. The method of claim 1, wherein at least one of the first or second fusion proteins further includes an oligomerization motif.

11. The method of claim 1, wherein at least one of the first and second fusion proteins includes a control polypeptide sequence, the function of which in the fusion protein is sensitive to at least one of stability of the fusion protein, folding of the fusion protein, and functional association of the fusion protein with a polymerase.

12. A method for detecting cleavage of a polypeptide by a proteolytic activity, comprising the method of claim 1, wherein one of either the first or second fusion proteins includes a potential proteolytic cleavage site which, when cleaved, alters expression of the reporter gene, and expression of the reporter gene is detected under conditions wherein the proteolytic activity is active in the host cells.

13. A method for identifying an antibody equivalent, comprising the method of claim 1, wherein the test polypeptide of one of either the first or second fusion proteins includes an epitope of interest and the other is a potential antibody equivalent, expression of the reporter gene being detected under conditions wherein an antibody equivalent binds to the epitope of interest.

14. A drug screening assay comprising the method of claim 1, wherein the expression of the reporter gene is detected in the presence of a test agent applied to the host cell and a test agent which alters the expression of the reporter gene is identified.

15. The method of claim 3, wherein the PID includes at least a portion of an RNA polymerase subunit.

16. The method of claim 7, wherein the nucleic acid library is a eukaryotic cDNA library, a eukaryotic genomic library, a prokaryotic genomic library, or a random or semi-random nucleic acid library.

17. The method of claim 8, wherein the DNA-binding domain includes a DNA binding portion of a transcriptional regulatory protein.

18. The method of claim 12, wherein the interaction trap system comprises a variegated population of the host cell collectively expressing a library of different potential proteolytic cleavage sites.

19. The method of claim 12, wherein the intreaction trap system comprises a variegated population of the host cell collectively expressing a library of genes including ones encoding potential proteolytic activities.

20. The method of claim 15, wherein the PID includes at least a portion of an $\alpha$ or $\omega$ polymerase subunit.

21. A kit for detecting interaction between a first test polypeptide and a second test polypeptide, the kit comprising:
 i. a first gene construct for encoding a first fusion protein, which first gene construct comprises:
  (1) transcriptional and translational elements which direct expression of the first fusion protein in a prokaryotic host cell,
  (2) a DNA sequence that encodes a DNA-binding domain and which is functionally associated with the transcriptional and translational elements of the first gene construct, and
  (3) a means for inserting a DNA sequence encoding a first test polypeptide into the first gene construct in such a manner that the first test polypeptide is expressed in-frame as part of the first fusion protein containing the DNA binding domain;
 ii. a second gene construct for encoding a second fusion protein, which second gene construct comprises:
  (1) transcriptional and translational elements which direct expression of the second fusion protein in a prokaryotic host cell,
  (2) a DNA sequence that encodes an activation tag, and which is functionally associated with the transcriptional and translational elements of the second gene construct, and
  (3) a means for inserting a DNA sequence encoding a second test polypeptide into the second vector in such a manner that the second test polypeptide is expressed in-frame as part of the second fusion protein containing the activation tag; and
 iii. a prokaryotic host cell containing a reporter gene having a binding site (DBD recognition element) for the DNA-binding domain, wherein the reporter gene expresses a detectable transcript or protein when the first and second fusion proteins interact.

22. The kit of claim 21, wherein the activation tag is a polymerase interaction domain (PID) which forms active RNA polymerase complexes in the host cell.

23. The kit of claim 21, wherein the host cell is selected from the group consisting of bacterial strains of Escherichia, Bacillus, Streptomyces, Pseudomonas, Salmonella, Serratia and Shigella.

24. The kit of claim 21, wherein the reporter gene encodes a gene product that gives rise to a detectable signal selected from the group consisting of: color, fluorescence, luminescence, a cell surface tag, cell viability, relief of a cell nutritional requirement, cell growth, and drug resistance.

25. The kit of claim 21, wherein the reporter gene encodes a gene product selected from the group consisting of the spectinomycin (spc) gene product, chloramphenicol acetyl transferase, luciferase, $\beta$-galactosidase and alkaline phosphatase.

26. The kit of claim 21, wherein the DNA-binding domain is a naturally occurring DNA binding protein.

27. The kit of claim 21, wherein the DNA-binding domain is an artificial polypeptide.

28. The kit of claim 21, wherein at least one of the first or second gene constructs further include a coding sequence for including an oligomerization motif in the fusion protein(s).

29. The kit of claim 21, wherein at least one of the first or second gene constructs further comprises a coding sequence for including a control polypeptide sequence in the fusion protein(s), the function of the control sequence in the fusion protein being sensitive to at least one of stability of the fusion protein, folding of the fusion protein, and functional association of the fusion protein with a polymerase.

30. The kit of claim 21, wherein the reporter gene is extrachrosomal.

31. The kit of claim 22, wherein the PID includes at least a portion of an RNA polymerase subunit.

32. The kit of claim 26, wherein the DNA-binding domain includes a DNA binding portion of a transcriptional regulatory protein.

33. The kit of claim 31, wherein the PID includes at least a portion of an $\alpha$ or $\omega$ polymerase subunit.

34. A method for identifying a nucleic acid encoding a test polypeptide which contacts another test polypeptide, comprising
 i. providing an interaction trap system including a variegated population of prokaryotic host cells which each include:
  (a) a reporter gene operably linked to a transcriptional regulatory sequence which includes a binding site (DBD recognition element) for a DNA-binding domain, (b) a first chimeric gene which encodes a first fusion protein, the first fusion protein including a DNA-binding domain and first test polypeptide, (c) a second chimeric gene which encodes a second fusion protein, the second fusion protein including an activation tag and a second test polypeptide, wherein interaction of the first fusion protein and second fusion protein in the host cell results in measurable change of expression of the reporter gene, and one of the first or second chimeric genes is present in the host cell population as a variegated population with respect to nucleic acid sequence encoding test polypeptides;

ii. measuring expression of the reporter gene; and iii. identifying nucleic acids which encode test polypeptides which increase expression of the reporter gene.

35. A method for detecting interaction between a test polypeptide and a DNA sequence, comprising i. providing a population of prokaryotic host cells which contain (a) a reporter gene operably linked to a transcriptional regulatory sequence which includes a binding site (DBD recognition element) for a DNA-binding domain, (b) a chimeric gene which encodes a fusion protein, the fusion protein including a test polypeptide and an activation tag, wherein interaction of the test polypeptide of the fusion protein with the DBD recognition element in the host cells results in a measurable change in expression of the reporter gene; and ii. measuring expression of the reporter gene, wherein the host cells comprise a variegated population of test polypeptides.

36. A method for detecting interaction between a test polypeptide and a DNA sequence, comprising i. providing a population of prokaryotic host cells which contain (a) a reporter gene operably linked to a transcriptional regulatory sequence which includes a binding site (DBD recognition element) for a DNA-binding domain, (b) a chimeric gene which encodes a fusion protein, the fusion protein including a test polypeptide and an activation tag, wherein interaction of the test polypeptide of the fusion protein with the DBD recognition element in the host cells results in a measurable change in expression of the reporter gene; and ii. measuring expression of the reporter gene, wherein the host cells-comprise a variegated population of DBD recognition elements.

* * * * *